(12) United States Patent
Keilhack et al.

(10) Patent No.: US 10,786,511 B2
(45) Date of Patent: Sep. 29, 2020

(54) METHOD FOR TREATING CANCER

(71) Applicants: Epizyme, Inc., Cambridge, MA (US); Eisai R&D Management Co., Ltd., Tokyo (JP)

(72) Inventors: Heike Keilhack, Belmont, MA (US); Brett Truitt, Cambridge, MA (US); Yuta Suzuki, Tokyo (JP); Tsukasa Murase, Tokyo (JP); Futoshi Shikata, Tokyo (JP)

(73) Assignees: Epizyme, Inc., Cambridge, MA (US); Eisai R&D Management Co., Ltd., Tokyo (JP)

( * ) Notice: Subject to any disclaimer, the term of this patent is extended or adjusted under 35 U.S.C. 154(b) by 24 days.

(21) Appl. No.: 15/527,375

(22) PCT Filed: Nov. 17, 2015

(86) PCT No.: PCT/US2015/061194
§ 371 (c)(1),
(2) Date: May 17, 2017

(87) PCT Pub. No.: WO2016/081523
PCT Pub. Date: May 26, 2016

(65) Prior Publication Data
US 2017/0360797 A1    Dec. 21, 2017

Related U.S. Application Data

(60) Provisional application No. 62/251,903, filed on Nov. 6, 2015, provisional application No. 62/166,572, filed on May 26, 2015, provisional application No. 62/080,985, filed on Nov. 17, 2014.

(51) Int. Cl.
| | | |
|---|---|---|
| *A61K 31/5377* | (2006.01) | |
| *A61K 9/00* | (2006.01) | |
| *A61K 9/20* | (2006.01) | |
| *A61K 33/06* | (2006.01) | |
| *A61K 9/28* | (2006.01) | |

(52) U.S. Cl.
CPC ........ *A61K 31/5377* (2013.01); *A61K 9/0053* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2077* (2013.01); *A61K 9/2095* (2013.01); *A61K 9/2846* (2013.01); *A61K 9/2893* (2013.01)

(58) Field of Classification Search
None
See application file for complete search history.

(56) References Cited

U.S. PATENT DOCUMENTS

| | | | |
|---|---|---|---|
| 6,248,363 B1 * | 6/2001 | Patel | A61K 9/1617 424/497 |
| 8,410,088 B2 | 4/2013 | Kuntz et al. | |
| 8,765,732 B2 | 7/2014 | Kuntz et al. | |
| 9,090,562 B2 | 7/2015 | Kuntz et al. | |
| 9,175,331 B2 | 11/2015 | Kuntz et al. | |
| 9,334,527 B2 | 5/2016 | Kuntz et al. | |
| 9,394,283 B2 * | 7/2016 | Kuntz | C07D 405/12 |
| 9,522,152 B2 | 12/2016 | Kuntz et al. | |
| 9,549,931 B2 | 1/2017 | Kuntz et al. | |
| 10,040,782 B2 * | 8/2018 | Kuntz | A61K 31/5377 |
| 2007/0026064 A1 * | 2/2007 | Yoder | A61K 9/2072 424/464 |
| 2010/0278921 A1 * | 11/2010 | Fischer | A61K 9/1652 424/489 |
| 2013/0040906 A1 | 2/2013 | Kuntz et al. | |
| 2013/0296325 A1 * | 11/2013 | Narang | A61K 9/2027 514/243 |
| 2014/0275081 A1 | 9/2014 | Kuntz et al. | |
| 2017/0065600 A1 | 3/2017 | Kuntz et al. | |
| 2017/0119780 A1 | 5/2017 | Kuntz et al. | |
| 2017/0252349 A1 | 9/2017 | Kuntz et al. | |

FOREIGN PATENT DOCUMENTS

| | | |
|---|---|---|
| WO | WO 2012/034132 A2 | 3/2012 |
| WO | WO 2012/118812 A2 | 9/2012 |
| WO | WO 2012/142504 A1 | 10/2012 |
| WO | WO 2012/142513 A1 | 10/2012 |
| WO | WO 2013/138361 A1 | 9/2013 |
| WO | WO 2013/155317 A1 | 10/2013 |
| WO | WO 2013/155464 A1 | 10/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100080 A1 | 6/2014 |
| WO | WO 2014/100646 A1 | 6/2014 |
| WO | WO 2014/100665 A1 | 6/2014 |
| WO | WO-2014100080 A1 * | 6/2014 ........... A61K 31/496 |

(Continued)

OTHER PUBLICATIONS

Winfield, Pharmaceutical Practice, Dosage forms, Churchill Livingstone, 2004, 213-218 (Year: 2004).*
Berge et al., Pharmaceutical Salts, Jan. 1977, Journal of Pharmaceutical Sciences, vol. 66, No. 1, 1-19.*
Lieberman et al., Pharmaceutical dosage forms: Tablets vol. 1—Diluents, Binders and Adhesives, Marcel Dekker, 1989, pp. 93-108.*
Rowe et al., Handbook of Pharmaceutical Excipients—Low substituted hydroxypropylcellulose, Pharmaceutical Press, 2009, pp. 322-324.*
Rowe et al., Handbook of Pharmaceutical Excipients—sodium starch glycolate, Pharmaceutical Press, 2009, pp. 663-666.*
Rowe et al., Handbook of Pharmaceutical Excipients—hydroxypropylcellulose, Pharmaceutical Press, 2009, pp. 317-322.*

(Continued)

*Primary Examiner* — Gigi G Huang
(74) *Attorney, Agent, or Firm* — Cooley LLP; Heidi A. Erlacher; Christine C. Pemberton

(57) ABSTRACT

The present invention relates to pharmaceutical compositions comprising inhibitor(s) of human histone methyltransferase EZH2, and methods of cancer therapy using the EZH2 inhibitor(s).

20 Claims, 19 Drawing Sheets

(56) References Cited

FOREIGN PATENT DOCUMENTS

| WO | WO 2014/144747 A1 | 9/2014 |
|---|---|---|
| WO | WO 2014/172044 A1 | 10/2014 |
| WO | WO 2015/010049 A1 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/195848 A1 | 12/2015 |
| WO | WO 2015/200650 A9 | 12/2015 |
| WO | WO 2016/061507 A1 | 4/2016 |

OTHER PUBLICATIONS

Rowe et al., Handbook of Pharmaceutical Excipients—Magnesium Stearate, Pharmaceutical Press, 2009, pp. 404-407.*

Rowe et al., Handbook of Pharmaceutical Excipients—Lactose, Spray-Dried, Pharmaceutical Press, 2009, pp. 376-378.*

Beringer, Remington: The Science and Practice of Pharmacy—Film Coating of Solid Dosage Forms, 21th edition, 2005, Lippencott, Williams, Wilkes, pp. 929-932.* clinicaltrials.gov Archive [online]. "Study of E7438 (EZH2 Histone Methyl Transferase [HMT] Inhibitor as a Single Agent in Subjects With Advanced Solid Tumors or With B Cell Lymphomas" Identifier NCT01897571, updated Mar. 27, 2014. Retrieved from: http://clinicaltrials.gov/archive/NCT01897571/2014_03_27; retrieved on Feb. 2, 2016 (8 pages).

Copeland, R. A. et al., "EZH2 Inhibitor EPZ-6438 (E7438) in Non-Hodgkin Lymphoma: Pre-Clinical Models and Early Clinical Observations," <URL: http://www.epizyme.com/wp-content/uploads/2014/08/ASH-Lymphoma-Conference-Copeland-FINAL.pdf>, Aug. 12, 2014.

Knutson, S. K. et al., "Selective Inhibition of EZH2 by EPZ-6438 Leads to Potent Antitumor Activity in EZH2-Mutant Non-Hodgkin Lymphoma," *Molecular Cancer Therapeutics* (2014), vol. 13, No. 4, pp. 842-854.

Sandeep, N. et al., "Immediate Drug Release Dosage Form: A Review," *Journal of Drug Delivery & Therapeutics* (2013), vol. 3, No. 2, pp. 155-161.

Garapaty-Rao, S. et al. (Nov. 2013) "Identification of EZH2 and EZH1 Small Molecule Inhibitors with Selective Impact on Diffuse Large B Cell Lymphoma Cell Growth" *Chem Biol*, 20:1329-1339.

Knutson, S.K. et al. (2012) "A Selective Inhibitor of EZH2 Blocks H3K27 Methylation and Kills Mutant Lymphoma Cells" *Nat Chem Biol*, 8:890-896.

Qi, W. et al. (2012) "Selective inhibition of Ezh2 by a small molecule inhibitor blocks tumor cells proliferation" *Proc Natl Acad Sci USA*, vol. 109, No. 52, p. 21360-21365.

Varambally, S. et al. (2002) "The Polycomb Group Protein EZH2 Is Involved in Progression of Prostate Cancer" *Nature*, 419:624-629.

* cited by examiner

| | Component | Manufacturing Step |
|---|---|---|
| Step 1 | EPZ-6438 Drug Substance<br>Lactose Monohydrate<br>Low-substituted Hydroxypropyl Cellulose | Mixing |
| Step 2 | Purified Water<br>Hydroxypropyl Cellulose | Granulation |
| Step 3 | | Drying |
| Step 4 | | Sizing |
| Step 5 | Low-substituted Hydroxypropyl Cellulose<br>Sodium Starch Glycolate<br>Magnesium Stearate | Lubrication |
| Step 6 | | Tableting |
| Step 7 | Opadry 03F45063 RED<br>Purified Water | Film-coating |

Fig. 8

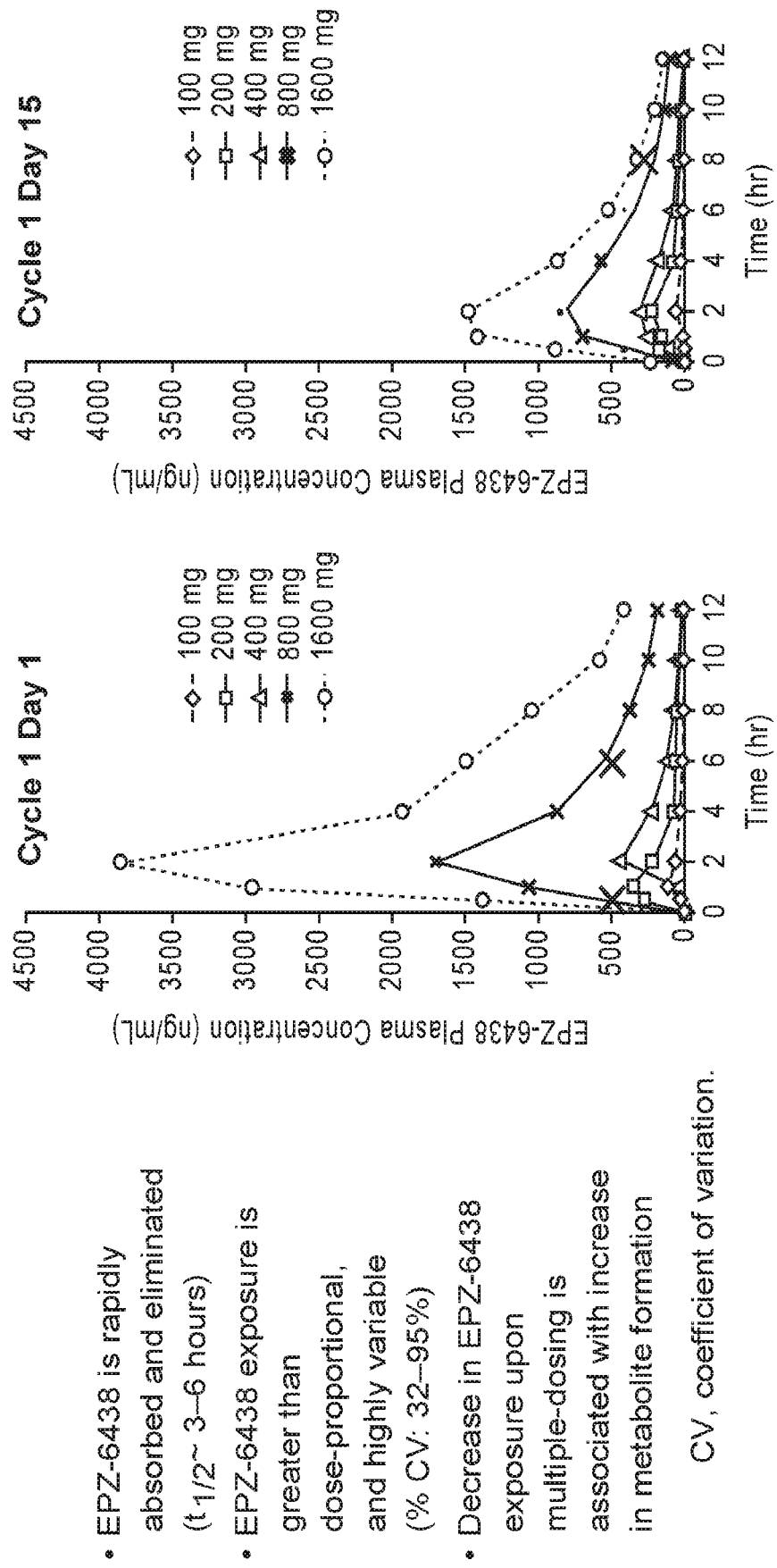

EPZ-6438 Pharmacodynamics in Skin

EPZ-6438 Pharmacodynamics in Skin

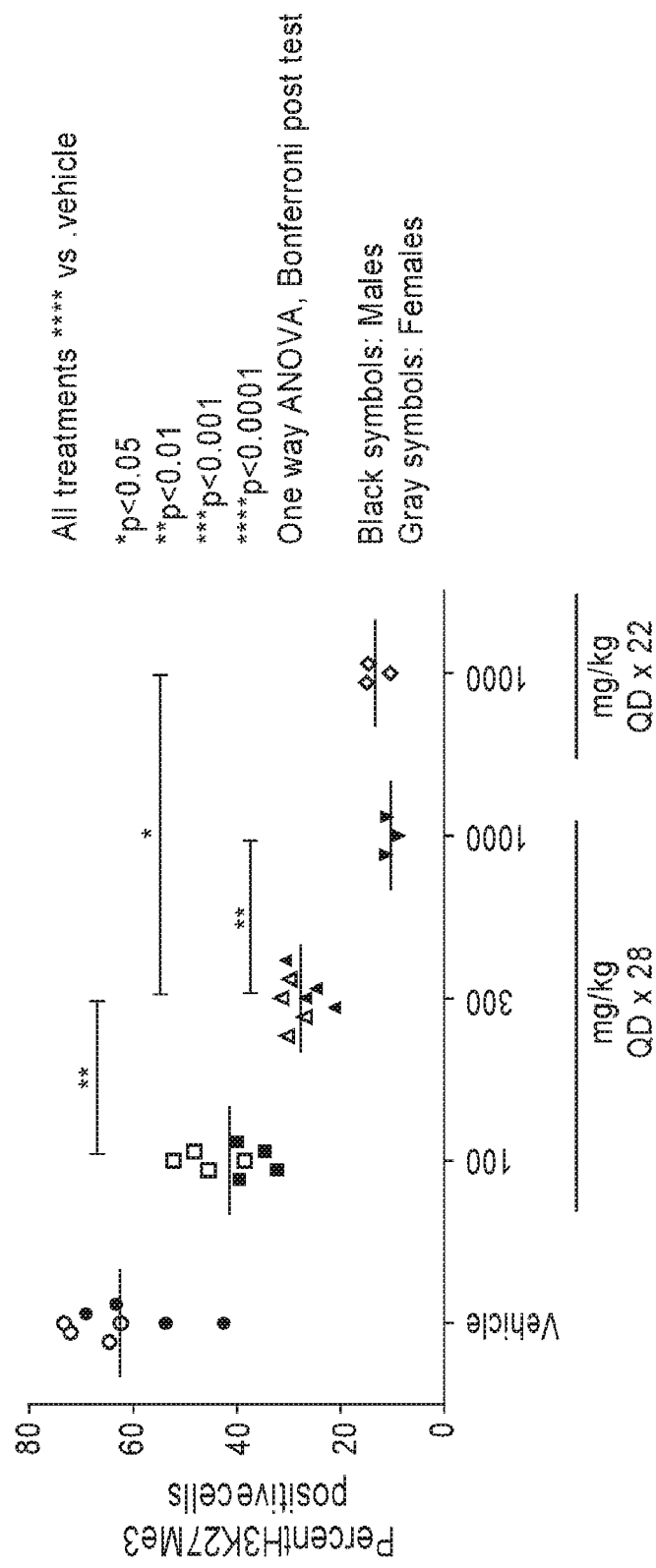

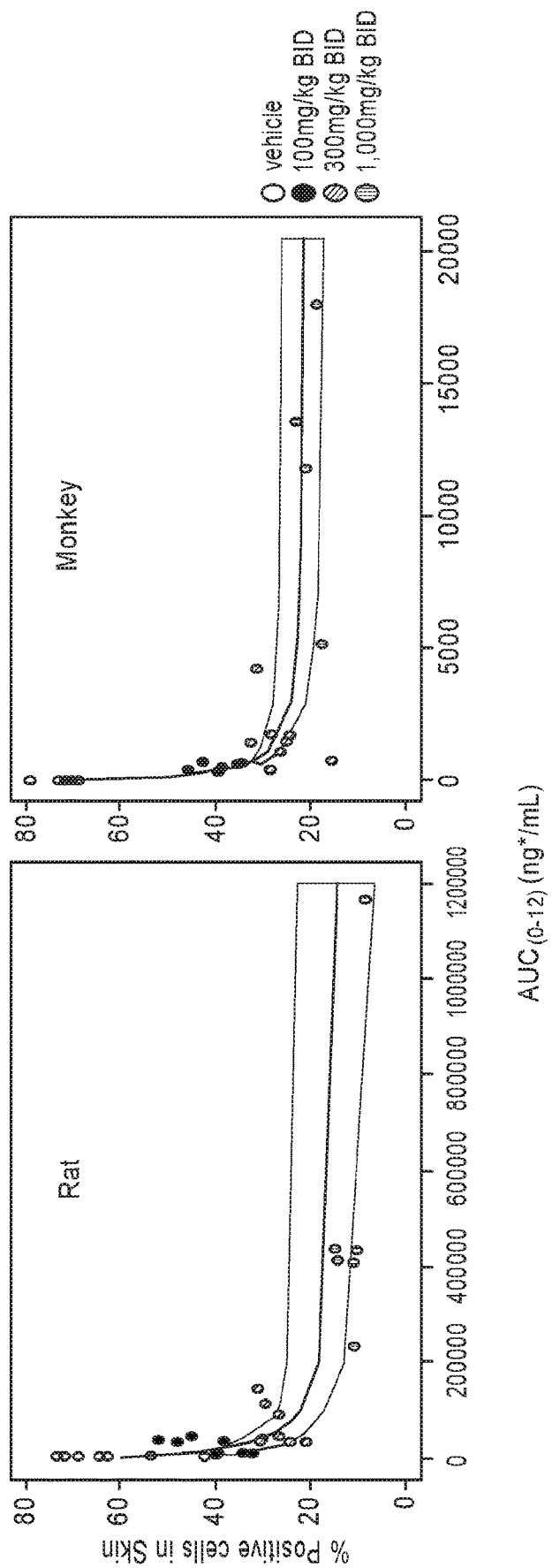

Advanced Image Analysis of H3K27 Trimethylation in Skin from Subjects Dosed with the EZH2 Inhibitor Tazemetostat Results Overview of Human Epidermal Layers An H&E image from skin delineating the multiple layers/stratum: (a) full epidermal layer, (b) basale, the single cell layer at the base of the epidermis and (c) spinosum.

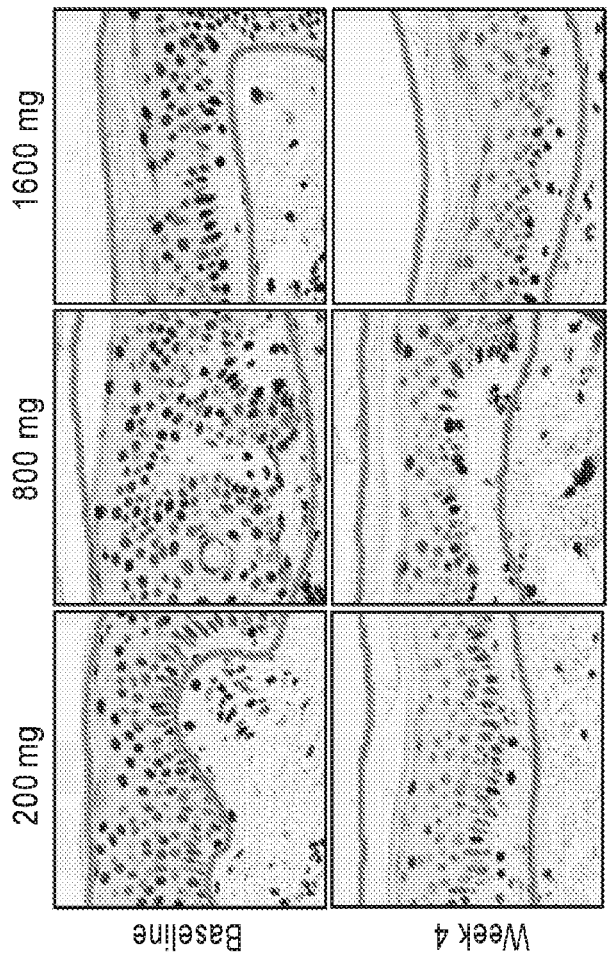

Fig. 16D

Advanced Image Analysis of H3K27 Trimethylation in Skin from Subjects Dosed with the EZH2 Inhibitor Tazemetostat Results Clinical H3K27me3 PD Skin biopsies at baseline exhibit uniform nuclear H3K27me3 throughout the epidermis. Post dose samples collected at four weeks show decreased staining in the stratum spinosum while the stratum basale appears minimally effected.

Fig. 16E

Advanced Image Analysis of H3K27 Trimethylation in Skin from Subjects Dosed with the EZH2 Inhibitor Tazemetostat

Results

Image Analysis

Image analysis identifies H3K27me3 positive (dark blue outline) and negative (aqua outlines) nuclei within the epidermal region of human skin.

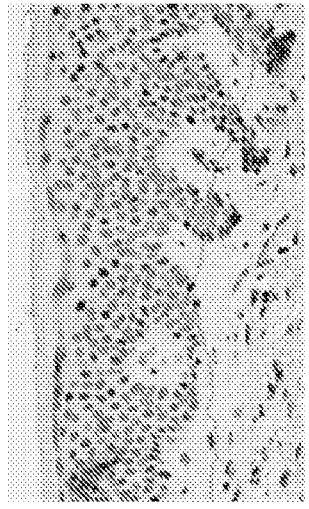 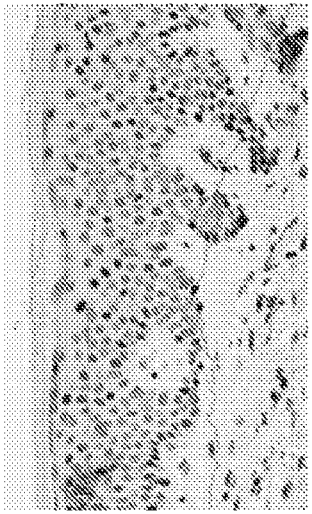

Nuclei outlined in green represent the segregated basale cells from the strata spinosum (red).

Advanced Image Analysis of H3K27 Trimethylation in Skin from Subjects Dosed with the EZH2 Inhibitor Tazemetostat

Results

Human PK/PD Relationship Analysis

Fractional change from baseline when comparing both dosage at Day 28 (left) and AUC (right) exhibits an improved correlation of H3K27me3 in the stratum spinosum vs. the epidermis.

METHOD FOR TREATING CANCER

RELATED APPLICATIONS

This application is a U.S. National Phase application, filed under 35 U.S.C. § 371, of International Application No. PCT/US2015/061194, filed Nov. 17, 2015, which claims the benefit of and priority to U.S. Patent Application Nos. 62/080,985, filed Nov. 17, 2014; 62/166,572, filed May 26, 2015; and 62/251,903, filed Nov. 6, 2015; the contents of each of which are hereby incorporated by reference in their entireties.

BACKGROUND OF THE INVENTION

EZH2, a histone methyltransferase, has been associated with various kinds of cancers. Specifically, mutations and and/or overactivity of EZH2 are found in a range of cancers, such as lymphomas, leukemias and breast cancer. There is an ongoing need for new agents as EZH2 inhibitors for use in anticancer treatment.

SUMMARY OF THE INVENTION

The present invention provides a method of treating cancer (e.g., a solid tumor, B cell lymphoma, or a cancer with aberrant H3-K27 methylation). The method comprises administering orally to a subject in need thereof a dosage form with a therapeutically effective amount of a compound of Formula (I) or a pharmaceutically acceptable salt thereof:

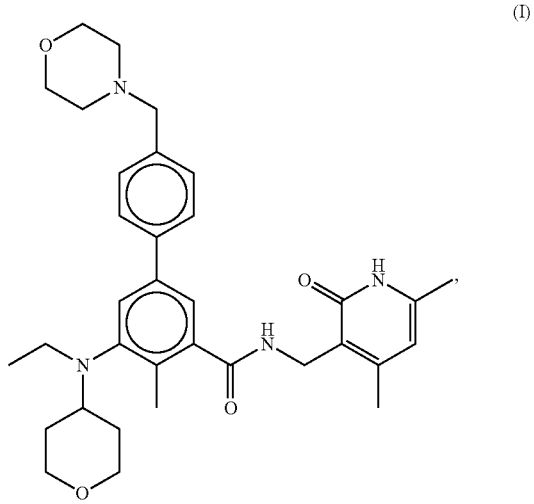

(I)

wherein said therapeutically effective amount is a single dose to provide a mean AUC(0-12) bioequivalent to a mean AUC(0-12) of from about 337 ng*hr/ml to about 18882 ng*hr/ml (e.g., from about 1720 ng*hr/ml to about 18882 ng*hr/ml, or from about 7798 ng*hr/ml to about 18882 ng*hr/ml) after administration to said subject. As used herein, the expressions "compound of Formula (I)," "Compound 1," and "EPZ-6438" all refer to the same compound and can be used interchangeably.

In another aspect, the present invention provides a method of treating cancer (e.g., an advanced solid tumor, B cell lymphoma, or a cancer with aberrant H3-K27 methylation), comprising administering orally to a subject in need thereof a dosage form with a therapeutically effective amount of EPZ-6438, wherein said therapeutically effective amount is a single dose to provide a mean AUC(0-12) bioequivalent to a mean AUC(0-12) of from about 4 ng*hr/ml to about 12 ng*hr/ml for each 1 mg of EPZ-6438 (e.g., from about 7 ng*hr/ml to about 12 ng*hr/ml for each 1 mg of EPZ-6438, from about 8 ng*hr/ml to about 12 ng*hr/ml for each 1 mg of EPZ-6438, from about 9 ng*hr/ml to about 12 ng*hr/ml for each 1 mg of EPZ-6438, or from about 9.7 ng*hr/ml to about 11.8 ng*hr/ml for each 1 mg of EPZ-6438).

In yet another aspect, the present invention provides a method of treating cancer (e.g., an advanced solid tumor, B cell lymphoma, or a cancer with aberrant H3-K27 methylation), comprising administering orally to a subject in need thereof a dosage form with a therapeutically effective amount of EPZ-6438, wherein said therapeutically effective amount provides a mean Cmax bioequivalent to a mean Cmax of from about 102 ng/ml to about 4125 ng/ml (e.g., from about 476 ng/ml to about 4125 ng/ml or from about 1730 ng/ml to about 4125 ng/ml).

In yet another aspect, the present invention provides a method of treating cancer (e.g., an advanced solid tumor, B cell lymphoma, or a cancer with aberrant H3-K27 methylation), comprising administering orally to a subject in need thereof a dosage form with a therapeutically effective amount of EPZ-6438, wherein said therapeutically effective amount is a single dose to provide a mean Cmax bioequivalent to a mean Cmax of from about 1.2 ng/ml to about 2.6 ng/ml for each 1 mg of EPZ-6438, e.g., from about 2.2 ng/ml to about 2.6 ng/ml for each 1 mg of EPZ-6438.

In still another aspect, the present invention provides a method of treating cancer (e.g., a solid tumor, B cell lymphoma, or a cancer with aberrant H3-K27 methylation), comprising administering orally to a subject in need thereof a dosage form with a therapeutically effective amount of EPZ-6438, wherein said therapeutically effective amount provides a median Tmax of from about 1 hour to about 2 hours.

The present invention also provides a method of inhibiting histone methyltransferase activity of EZH2 or a mutant thereof, comprising administering orally to a subject in need thereof a dosage form with a therapeutically effective amount of EPZ-6438, wherein said therapeutically effective amount provides a mean AUC(0-12) of at least about 1170 ng*hr/ml, e.g., at least about 4421 ng*hr/ml after administration to the subject.

Further, the present invention also provides a method of inhibiting histone methyltransferase activity of EZH2 or a mutant thereof, comprising administering orally to a subject in need thereof a dosage form with a therapeutically effective amount of EPZ-6438, wherein said therapeutically effective amount is a single dose to provide a mean AUC (0-12) bioequivalent to a mean AUC(0-12) of from about 337 ng*hr/ml to about 18882 ng*hr/ml (e.g., from about 1720 ng*hr/ml to about 18882 ng*hr/ml, or from about 7798 ng*hr/ml to about 18882 ng*hr/ml) after administration to the subject.

In yet another aspect, the present invention also provides a method of inhibiting histone methyltransferase activity of EZH2 or a mutant thereof, comprising administering orally to a subject in need thereof a dosage form with a therapeutically effective amount of EPZ-6438, wherein said therapeutically effective amount is a single dose to provide a mean AUC(0-12) bioequivalent to a mean AUC(0-12) of from about 4 ng*hr/ml to about 12 ng*hr/ml for each 1 mg of EPZ-6438 (e.g., from about 7 ng*hr/ml to about 12 ng*hr/ml for each 1 mg of EPZ-6438, from about 8 ng*hr/ml to about 12 ng*hr/ml for each 1 mg of EPZ-6438, from about 9 ng*hr/ml to about 12 ng*hr/ml for each 1 mg of EPZ-6438, or from about 9.7 ng*hr/ml to about 11.8 ng*hr/ml for each 1 mg of EPZ-6438).

In yet another aspect, the present invention also relates to a method of inhibiting histone methyltransferase activity of EZH2 or a mutant thereof, comprising administering orally to a subject in need thereof a dosage form with a therapeutically effective amount of EPZ-6438, wherein said single dose provides a mean Cmax bioequivalent to a mean Cmax of from about 102 ng/ml to about 4125 ng/ml (e.g., from about 476 ng/ml to about 4125 ng/ml or from about 1730 ng/ml to about 4125 ng/ml).

In still another aspect, the present invention relates to a method of inhibiting histone methyltransferase activity of EZH2 or a mutant thereof, comprising administering orally to a subject in need thereof a dosage form with a therapeutically effective amount of EPZ-6438, wherein said therapeutically effective amount is a single dose to provide a mean Cmax bioequivalent to a mean Cmax of from about 1.2 ng/ml to about 2.6 ng/ml for each 1 mg of EPZ-6438, e.g., from about 2.2 ng/ml to about 2.6 ng/ml for each 1 mg of EPZ-6438.

The present invention also relates to a method of inhibiting histone methyltransferase activity of EZH2 or a mutant thereof, comprising administering orally to a subject in need thereof a dosage form with a therapeutically effective amount of EPZ-6438, wherein said therapeutically effective amount provides a median Tmax of from about 1 hour to about 2 hours.

Still, the present invention relates to a method of treating an advanced solid tumor or B cell lymphoma, comprising administering orally to a subject in need thereof a dosage form with a therapeutically effective amount of EPZ-6438, wherein said therapeutically effective amount provides a mean AUC(0-12) of at least about 1170 ng*hr/ml, e.g., at least about 4421 ng*hr/ml after administration to the subject.

The present invention also provides an oral dosage form for treating cancer (e.g., a solid tumor, B cell lymphoma, or a cancer with aberrant H3-K27 methylation) comprising a therapeutically effective amount of EPZ-6438, and at least one pharmaceutically acceptable carrier or excipient, wherein said therapeutically effective amount is a single dose to provide a mean AUC(0-12) bioequivalent to a mean AUC(0-12) of from about 337 ng*hr/ml to about 18882 ng*hr/ml (e.g., from about 1720 ng*hr/ml to about 18882 ng*hr/ml, or from about 7798 ng*hr/ml to about 18882 ng*hr/ml) after administration to a human subject.

In another aspect, an oral dosage form is provided herein for treating an advanced solid tumor or B cell lymphoma, comprising a therapeutically effective amount of EPZ-6438, and at least one pharmaceutically acceptable carrier or excipient, wherein said therapeutically effective amount is a single dose to provide a mean AUC(0-12) bioequivalent to a mean AUC(0-12) of from about 4 ng*hr/ml to about 12 ng*hr/ml for each 1 mg of EPZ-6438 (e.g., from about 7 ng*hr/ml to about 12 ng*hr/ml for each 1 mg of EPZ-6438, from about 8 ng*hr/ml to about 12 ng*hr/ml for each 1 mg of EPZ-6438, from about 9 ng*hr/ml to about 12 ng*hr/ml for each 1 mg of EPZ-6438, or from about 9.7 ng*hr/ml to about 11.8 ng*hr/ml after for each 1 mg of EPZ-6438).

In another aspect, provided herewith is an oral dosage form for treating an advanced solid tumor or B cell lymphoma, comprising a therapeutically effective amount of EPZ-6438, and at least one pharmaceutically acceptable carrier or excipient, wherein said therapeutically effective amount provides a mean Cmax bioequivalent to a mean Cmax of from about 102 ng/ml to about 4125 ng/ml (e.g., from about 476 ng/ml to about 4125 ng/ml or from about 1730 ng/ml to about 4125 ng/ml).

In yet another aspect, provided herewith is a dosage form for treating an advanced solid tumor or B cell lymphoma, comprising a therapeutically effective amount of EPZ-6438, and at least one pharmaceutically acceptable carrier or excipient, wherein said therapeutically effective amount is a single dose to provides a mean Cmax bioequivalent to a mean Cmax of from about 1.2 ng/ml to about 2.6 ng/ml for each 1 mg of EPZ-6438, e.g., from about 2.2 ng/ml to about 2.6 ng/ml for each 1 mg of EPZ-6438.

Also provided herewith is an oral dosage form for treating an advanced solid tumor or B cell lymphoma, comprising a therapeutically effective amount of EPZ-6438, and at least one pharmaceutically acceptable carrier or excipient, wherein said therapeutically effective amount provides a mean AUC(0-12) of at least about 1170 ng*hr/ml, e.g., at least about 4421 ng*hr/ml after administration to a human subject.

The present invention also relates to a solid pharmaceutical formulation comprising a therapeutic agent and one or more pharmaceutically acceptable excipients, wherein the therapeutic agent is Compound 1, a salt thereof, and a combination thereof, and the concentration of the therapeutic agent in the formulation is equivalent to about 35-65 wt. % Compound 1. In certain embodiments, the concentration of the therapeutic agent in the formulation is equivalent to about 1-99 wt. %, 10-90%, 20-80%, 30-70%, or 35-65 wt. % Compound 1. In certain embodiments, the concentration of the therapeutic agent in the formulation is equivalent to about 50 wt. %, 55 wt. % or 60 wt. % Compound 1. In one embodiment, the pharmaceutical formulation is in a solid unit dosage form. In one embodiment, the pharmaceutical formulation is an oral unit dosage formulation. In one embodiment, the pharmaceutical formulation is in the form of a tablet.

The present invention also relates to a solid pharmaceutical formulation comprising a therapeutic agent (e.g., Compound 1 or a salt thereof, or a combination thereof) and one or more pharmaceutically acceptable excipients selected from sodium starch glycolate, carmellose, carmellose calcium, croscarmellose sodium, or low-substituted hydroxypropylcellulose, and a combination thereof. In one embodiment, the excipients are selected from sodium starch glycolate, carmellose, carmellose calcium, or croscarmellose sodium, and a combination thereof. In one embodiment, the excipients are selected from sodium starch glycolate, or carmellose, and a combination thereof. In one embodiment, the solid pharmaceutical formulation further includes lactose, hydroxypropyl cellulose, or magnesium stearate or a combination thereof.

The present invention also relates to a solid pharmaceutical composition comprising a therapeutic agent and means for achieving immediate release of the therapeutic agent, wherein the therapeutic agent is selected from Compound 1, a salt thereof, and a combination thereof.

In another aspect, the present invention relates to a process of making the pharmaceutical formulation or composition disclosed herein. The process includes a) mixing a therapeutic agent, a diluent, a disintegrant and optionally a lubricant to form a first mixture, wherein the therapeutic agent is selected from the group consisting of Compound 1, a salt thereof, and a combination thereof. The process optionally includes one or more of the following steps:

b) adding an aqueous solution, or an organic solvent-based solution (e.g. IPA, EtOH, etc.), or an organic/aqueous mixture (e.g. 1:1 EtOH:Water) comprising a binder to the first mixture to form a second mixture;

c) granulating the second mixture to form wet granulates;

d) drying the wet granulates to form dried granulates;

e) size screening the dried granulates to obtain sized granulates;

f) mixing the sized granulates with a lubricant, and a second disintegrant to form a third mixture;

g) compressing the third mixture to form tablets; and h) applying a coating suspension to the tablets to generate film-coated tablets.

In certain embodiments, the present invention relates to a process of making the pharmaceutical formulation disclosed herein. The process includes a) mixing a therapeutic agent, a diluent, and a disintegrant to form a first mixture, wherein the therapeutic agent is selected from the group consisting of Compound 1, a salt thereof, and a combination thereof.

The process optionally includes one or more of the following steps:

b) granulating the first mixture to dry granulates;

e) size screening the dry granulates;

f) mixing the sized granulates with a lubricant, and a second disintegrant to form a third mixture;

g) compressing the third mixture to form tablets; and h) applying a coating suspension to the tablets to generate film-coated tablets.

Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Any of the above aspects and embodiments can be combined with any other aspect or embodiment.

Other features and advantages of the invention will be apparent from the following detailed description and claims.

BRIEF DESCRIPTION OF THE DRAWINGS

FIG. 8 is a flowchart of an embodiment of the manufacturing process for film-coated EPZ-6438 tablets.

FIG. 15A is a series of plots of mean EPZ-6438 plasma concentration vs time profiles following twice-daily administration of EPZ-6438 at day 1 and at day 15.

FIGS. 16A-16F are a series of plots or images from an advanced image analysis of H3K27 trimethylation in skin from subjects dosed with the EZH2 inhibitor Tazemetostat.

DETAILED DESCRIPTION OF THE INVENTION

Figure 1A:
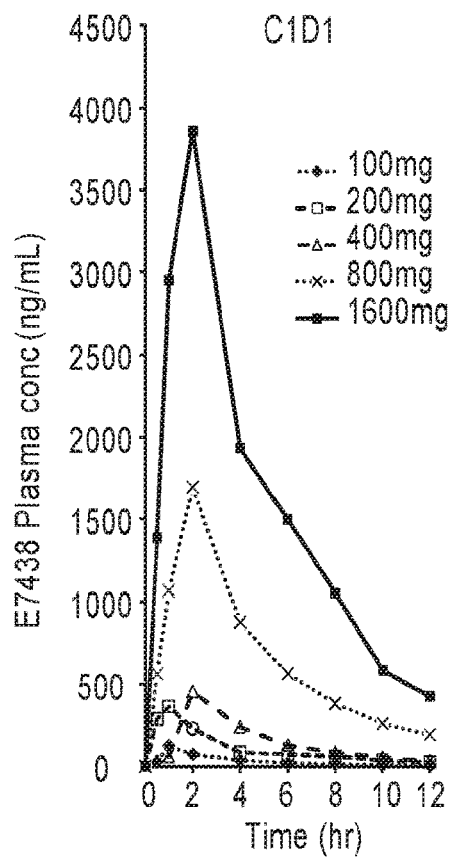
FIGS. 1A and 1B are plots of mean EPZ-6438 plasma concentration vs time profiles following twice-daily administration of EPZ-6438: (A) at day 1 and (B) at day 15.

Histone methyltransferases (HMTs) play a crucial role in the regulation of gene expression. In particular, HMTs are involved in the regulation of cellular division and of cellular differentiation. HMTs mediate the methylation of histones associated with particular genes. Depending on the amino acid residues that are methylated, the methylation event can either signal a silencing event or an activation event for the associated gene. Examples of a silencing mark include the trimethylation of H3K27; whereas, trimethylation of H3K4 results in a gene activating signal. Many cell cycle check point regulators and tumor suppressor genes exist in a "bivalent" state, wherein these contain both activating histone modifications (e.g. H3K27me3) and suppressing histone modifications (e.g. H3K4me3). Genes in a bivalent state are poised to undergo either activation or suppression depending on external factors. EZH2 regulates bivalent genes involved in B-cell differentiation and maturation, including CDKN1, PRDM1, and IRF4.

EZH2 is a histone methyltransferase that is the catalytic subunit of the PRC2 complex which catalyzes the mono-through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

EZH2 methylation activity plays an important role in the regulation and activation of germinal center B-cells. EZH2 protein levels increase following the activation of B-cells. Following activation, B-cells take residence in the germinal center of lymphoid organs, wherein somatic hypermutation occurs, a process associated with the repression of anti-apoptotic genes and check point regulators. EZH2 methylating events target genes that are involved in B-cell proliferation, differentiation and maturation, including CDKN1A (role in cellular proliferation), PRDM1 (role in B-cell differentiation) and IRF4 (role in B-cell differentiation).

Following the maturation and exit of B-cells from the germinal center, there is a reduction of the levels of EZH2 within the B-cells. However, EZH2 presence and activity after B-cell maturation is associated with several kinds of lymphomas including germinal center B-cell lymphoma, among others. Aberrant activation of EZH2 is found in three common subtypes of germinal cell lymphomas: follicular lymphoma (FL), germinal center B-cell like diffuse large B-cell lymphoma (GCB DLBCL), and Burkitt's lymphoma. Aberrant activation of EZH2 is also found in Primary Mediastinal Large B-Cell Lymphoma (PMBCL).

Genetic alterations within the EZH2 gene are associated with altered histone methylation patterns. For example, certain point mutations in EZH2 are associated with altered methylation of H3K4 in DLBCL; furthermore, chromosomal translocation and fusion, SSX:SS18, is associated with altered H3K27 methylation in synovial sarcoma. EZH2 mutations leading to the conversion of amino acid Y641 (equivalent to Y646, catalytic domain), to either F, N, H, S or C results in hypertrimethylation of H3K27 and drives lymphomagenesis. Additional genetic alterations that affect the methylation of H3K27 include EZH2 SET-domain mutations, overexpression of EZH2, overexpression of other PRC2 subunits, loss of function mutations of histone acetyl transferases (HATs), and loss of function of MLL2. Cells that are heterozygous for EZH2 Y646 mutations result in hypertrimethylation of H3K27 relative to cells that are homozygous wild-type (WT) for the EZH2 protein, or to cells that are homozygous for the Y646 mutation.

EPZ-6438 (Compound 1) is a small molecule inhibitor of EZH2, the catalytic subunit of the polycomb repressive complex 2 that methylates H3K27. Hypertrimethylation of H3K27 (H3K27Me3) appears tumorigenic in various malignancies, including subsets of Non-Hodgkin Lymphoma (NHL) with mutant EZH2. Inhibition of H3K27Me3 with EPZ-6438 leads to killing of EZH2 mutant lymphoma cells and other EZH2 inhibitors show activity in models of mutant and WT EZH2 NHL. In addition, tumors with loss of INI1, a subunit of the SW1-SNF chromatin remodeling complex, appeared dependent on EZH2. EPZ-6438 was shown to induce apoptosis and differentiation of INI1-deleted malignant rhabdoid tumor (MRT) models in vitro and in MRT xenograft-bearing mice.

This invention is based on, at least in part, discovery that Enhancer of Zeste Homolog 2 (EZH2) inhibitors may effectively treat cancer(s), for example cancer(s) that are characterized by aberrant H3-K27 methylation.

An aspect of the present invention relates to a method for treating or alleviating a method of treating cancer (e.g., a solid tumor, B cell lymphoma, or a cancer with aberrant H3-K27 methylation). The method comprises by administering orally to a subject in need thereof a dosage form with a therapeutically effective amount of a compound of Formula (I) or a pharmaceutically acceptable salt thereof:

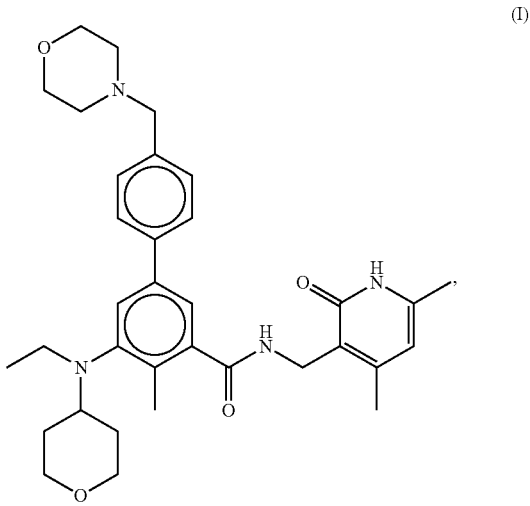

(I)

wherein said therapeutically effective amount is a single dose to provide a mean AUC(0-12) bioequivalent to a mean AUC(0-12) of from about 337 ng*hr/ml to about 18882 ng*hr/ml (e.g., from about 1720 ng*hr/ml to about 18882 ng*hr/ml, or from about 7798 ng*hr/ml to about 18882 ng*hr/ml) after administration to said subject.

As used herein, the expressions "compound of Formula (I)," "Compound 1," and "EPZ-6438" all refer to the same compound and can be used interchangeably.

In another aspect, the present invention provides a method of treating cancer (e.g., an advanced solid tumor, B cell lymphoma, or a cancer with aberrant H3-K27 methylation), comprising administering orally to a subject in need thereof a dosage form with a therapeutically effective amount of EPZ-6438, wherein said therapeutically effective amount is a single dose to provide a mean AUC(0-12) bioequivalent to a mean AUC(0-12) of from about 4 ng*hr/ml to about 12 ng*hr/ml for each 1 mg of EPZ-6438 (e.g., from about 7 ng*hr/ml to about 12 ng*hr/ml for each 1 mg of EPZ-6438, from about 8 ng*hr/ml to about 12 ng*hr/ml for each 1 mg of EPZ-6438, from about 9 ng*hr/ml to about 12 ng*hr/ml for each 1 mg of EPZ-6438, or from about 9.7 ng*hr/ml to about 11.8 ng*hr/ml for each 1 mg of EPZ-6438).

In yet another aspect, the present invention provides a method of treating cancer (e.g., an advanced solid tumor, B cell lymphoma, or a cancer with aberrant H3-K27 methylation), comprising administering orally to a subject in need thereof a dosage form with a therapeutically effective amount of EPZ-6438, wherein said therapeutically effective amount provides a mean Cmax bioequivalent to a mean Cmax of from about 102 ng/ml to about 4125 ng/ml (e.g., from about 476 ng/ml to about 4125 ng/ml or from about 1730 ng/ml to about 4125 ng/ml).

In yet another aspect, the present invention provides a method of treating cancer (e.g., an advanced solid tumor, B cell lymphoma, or a cancer with aberrant H3-K27 methylation), comprising administering orally to a subject in need thereof a dosage form with a therapeutically effective amount of EPZ-6438, wherein said therapeutically effective amount is a single dose to provide a mean Cmax bioequivalent to a mean Cmax of from about 1.2 ng/ml to about 2.6 ng/ml for each 1 mg of EPZ-6438, e.g., from about 2.2 ng/ml to about 2.6 ng/ml for each 1 mg of EPZ-6438.

In still another aspect, the present invention provides a method of treating cancer (e.g., a solid tumor, B cell lymphoma, or a cancer with aberrant H3-K27 methylation), comprising administering orally to a subject in need thereof a dosage form with a therapeutically effective amount of EPZ-6438, wherein said therapeutically effective amount provides a median Tmax of from about 1 hour to about 2 hours.

The present invention also provides a method of inhibiting histone methyltransferase activity of EZH2 or a mutant thereof, comprising administering orally to a subject in need thereof a dosage form with a therapeutically effective amount of EPZ-6438, wherein said therapeutically effective amount provides a mean AUC(0-12) of at least about 1170 ng*hr/ml, e.g., at least about 4421 ng*hr/ml after administration to the subject.

Further, the present invention also provides a method of inhibiting histone methyltransferase activity of EZH2 or a mutant thereof, comprising administering orally to a subject in need thereof a dosage form with a therapeutically effective amount of EPZ-6438, wherein said therapeutically effective amount is a single dose to provide a mean AUC(0-12) bioequivalent to a mean AUC(0-12) of from about 337 ng*hr/ml to about 18882 ng*hr/ml (e.g., from about 1720 ng*hr/ml to about 18882 ng*hr/ml, or from about 7798 ng*hr/ml to about 18882 ng*hr/ml) after administration to the subject.

In yet another aspect, the present invention also provides a method of inhibiting histone methyltransferase activity of EZH2 or a mutant thereof, comprising administering orally to a subject in need thereof a dosage form with a therapeutically effective amount of EPZ-6438, wherein said therapeutically effective amount is a single dose to provide a mean AUC(0-12) bioequivalent to a mean AUC(0-12) of from about 4 ng*hr/ml to about 12 ng*hr/ml for each 1 mg of EPZ-6438 (e.g., from about 7 ng*hr/ml to about 12 ng*hr/ml for each 1 mg of EPZ-6438, from about 8 ng*hr/ml to about 12 ng*hr/ml for each 1 mg of EPZ-6438, from about 9 ng*hr/ml to about 12 ng*hr/ml for each 1 mg of EPZ-6438, or from about 9.7 ng*hr/ml to about 11.8 ng*hr/ml for each 1 mg of EPZ-6438).

In yet another aspect, the present invention also relates to a method of inhibiting histone methyltransferase activity of EZH2 or a mutant thereof, comprising administering orally to a subject in need thereof a dosage form with a therapeutically effective amount of EPZ-6438, wherein said single dose provides a mean Cmax bioequivalent to a mean Cmax of from about 102 ng/ml to about 4125 ng/ml (e.g., from about 476 ng/ml to about 4125 ng/ml or from about 1730 ng/ml to about 4125 ng/ml).

In still another aspect, the present invention relates to a method of inhibiting histone methyltransferase activity of EZH2 or a mutant thereof, comprising administering orally to a subject in need thereof a dosage form with a therapeutically effective amount of EPZ-6438, wherein said therapeutically effective amount is a single dose to provide a mean Cmax bioequivalent to a mean Cmax of from about 1.2 ng/ml to about 2.6 ng/ml for each 1 mg of EPZ-6438, e.g., from about 2.2 ng/ml to about 2.6 ng/ml for each 1 mg of EPZ-6438.

The present invention also relates to a method of inhibiting histone methyltransferase activity of EZH2 or a mutant thereof, comprising administering orally to a subject in need thereof a dosage form with a therapeutically effective amount of EPZ-6438, wherein said therapeutically effective amount provides a median Tmax of from about 1 hour to about 2 hours.

Still, the present invention relates to a method of treating an advanced solid tumor or B cell lymphoma, comprising administering orally to a subject in need thereof a dosage form with a therapeutically effective amount of EPZ-6438, wherein said therapeutically effective amount provides a mean AUC(0-12) of at least about 1170 ng*hr/ml, e.g., at least about 4421 ng*hr/ml after administration to the subject.

The present invention also provides an oral dosage form for treating cancer (e.g., a solid tumor, B cell lymphoma, or a cancer with aberrant H3-K27 methylation) comprising a therapeutically effective amount of EPZ-6438, and at least one pharmaceutically acceptable carrier or excipient, wherein said therapeutically effective amount is a single dose to provide a mean AUC(0-12) bioequivalent to a mean AUC(0-12) of from about 337 ng*hr/ml to about 18882 ng*hr/ml (e.g., from about 1720 ng*hr/ml to about 18882 ng*hr/ml, or from about 7798 ng*hr/ml to about 18882 ng*hr/ml) after administration to a human subject.

In another aspect, an oral dosage form is provided herein for treating an advanced solid tumor or B cell lymphoma, comprising a therapeutically effective amount of EPZ-6438, and at least one pharmaceutically acceptable carrier or excipient, wherein said therapeutically effective amount is a single dose to provide a mean AUC(0-12) bioequivalent to a mean AUC(0-12) of from about 4 ng*hr/ml to about 12 ng*hr/ml for each 1 mg of EPZ-6438 (e.g., from about 7 ng*hr/ml to about 12 ng*hr/ml for each 1 mg of EPZ-6438, from about 8 ng*hr/ml to about 12 ng*hr/ml for each 1 mg of EPZ-6438, from about 9 ng*hr/ml to about 12 ng*hr/ml for each 1 mg of EPZ-6438, or from about 9.7 ng*hr/ml to about 11.8 ng*hr/ml after for each 1 mg of EPZ-6438).

In another aspect, provided herewith is an oral dosage form for treating an advanced solid tumor or B cell lymphoma, comprising a therapeutically effective amount of EPZ-6438, and at least one pharmaceutically acceptable carrier or excipient, wherein said therapeutically effective amount provides a mean Cmax bioequivalent to a mean Cmax of from about 102 ng/ml to about 4125 ng/ml (e.g., from about 476 ng/ml to about 4125 ng/ml or from about 1730 ng/ml to about 4125 ng/ml).

In yet another aspect, provided herewith is a dosage form for treating an advanced solid tumor or B cell lymphoma, comprising a therapeutically effective amount of EPZ-6438, and at least one pharmaceutically acceptable carrier or excipient, wherein said therapeutically effective amount is a single dose to provides a mean Cmax bioequivalent to a mean Cmax of from about 1.2 ng/ml to about 2.6 ng/ml for each 1 mg of EPZ-6438, e.g., from about 2.2 ng/ml to about 2.6 ng/ml for each 1 mg of EPZ-6438.

Also provided herewith is an oral dosage form for treating an advanced solid tumor or B cell lymphoma, comprising a therapeutically effective amount of EPZ-6438, and at least one pharmaceutically acceptable carrier or excipient, wherein said therapeutically effective amount provides a mean AUC(0-12) of at least about 1170 ng*hr/ml, e.g., at least about 4421 ng*hr/ml after administration to a human subject.

The expression "bioequivalent" or "bioequivalence" is a term of art and is intended to be defined in accordance with Approved Drug Products with Therapeutic Equivalence Evaluations, 34$^{th}$ Edition, which is published by the U.S Department of Health and Human Services, and is commonly known as the "Orange Book". Bioequivalence of different formulation of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. Detailed guidelines for establishing the bioequivalence of a formulation with a reference formulation have been published by the FDA Office of Generic Drugs, Division of Bioequivalence.

Two dosage forms whose rate and extent of absorption differ by −20%/+25% or less are generally considered "bioequivalent". Another approach for average bioequivalence involves the calculation of a 90% confidence interval for the ratio of the averages (population geometric means) of the measures for the test and reference products. To establish BE, the calculated confidence interval should fall within usually 80-125% for the ratio of the product averages. In addition to this general approach, the others approach, including (1) logarithmic transformation of pharmacokinetic data, (2) methods to evaluate sequence effects and (3) methods to evaluate outlier data, may be useful for the establishment of bioequivalence. For example, in the above (1) the confidence interval should fall within usually 80-125% for the difference in the mean value of the logarithmic converted PK parameter.

The present invention relates to a pharmaceutical formulation comprising a therapeutic agent and one or more pharmaceutically acceptable excipients, wherein the therapeutic agent Compound 1:

("Compound 1")

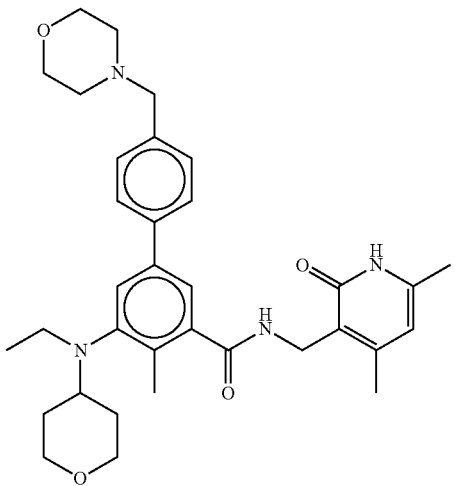

or a salt thereof, or a combination thereof, and the concentration of the therapeutic agent in the formulation is equivalent to about 35-65 wt. % Compound 1.

The present invention relates to an immediate-release formulation comprising Compound 1 or a salt thereof. In embodiments, the immediate-release formulation releases the therapeutic agent within short time (e.g. no less than 80% of the therapeutic agent included in the formulation being released after 60 min.). In certain embodiments, the immediate-release formulation releases at least 90%, or at least 80%, or at least 70%, or at least 60% of the therapeutic agent after 60 min in a medium having a pH value ranging between 1 and 6.8 (e.g., pH=1.2). In certain embodiments, the immediate-release formulation releases at least 90%, or at least 80%, or at least 70%, or at least 60% of the therapeutic agent after 45 min in a medium having a pH value ranging between 1 and 6.8 (e.g., pH=1.2). In certain embodiments, the immediate-release formulation is in the form of a tablet.

The formulation of the invention can include one or more of the following features when applicable:

For example, the concentration of the therapeutic agent in the formulation is equivalent to about 40 wt. % to about 60 wt. % Compound 1.

For example, the concentration of the therapeutic agent in the formulation is equivalent to about 45 wt. % to about 55 wt. % Compound 1.

For example, the concentration of the therapeutic agent in the formulation is equivalent to about 47 wt. % to about 50 wt. % Compound 1.

For example, the therapeutic agent is a salt of Compound 1, e.g., a hydrobromide (HBr) salt, such as a monohydrobromide salt.

For example, the one or more pharmaceutically acceptable excipients include a diluent(s), a disintegrant(s), and a binder(s).

For example, the formulation comprises about 10 wt. % to about 20 wt. % diluent, e.g., about 10 wt. %, 11 wt. %, 12 wt. %, 13 wt. %, 14 wt. %, 15 wt. %, 16 wt. %, 17 wt. %, 18 wt. %, 19 wt. %, or 20 wt. %.

For example, the total concentration of the therapeutic agent and diluent is about 60-80 wt. %, e.g., about 65 wt. %, 67.5 wt. %, 70 wt. %, 72.5 wt. %, 75 wt. %, or 80 wt. %.

For example, the diluent is lactose monohydrate.

For example, the formulation comprises about 15 wt. % to about 25 wt. % disintegrant, e.g., about 15 wt. %, 16 wt. %, 17 wt. %, 18 wt. %, 19 wt. %, 20 wt. %, 21 wt. %, 22 wt. %, 23 wt. %, 24 wt. %, or 25 wt. %.

For example, the disintegrant comprises low-substituted hydroxypropyl cellulose, sodium starch glycolate, or a combination thereof.

For example, the formulation comprises about 1 wt. % to about 10 wt. % binder, e.g., about 1 wt. %, 2 wt. %, 3 wt. %, 4 wt. %, 5 wt. %, 6 wt. %, 7 wt. %, 8 wt. %, 9 wt. %, or 10 wt. %.

For example, the binder is hydroxypropyl cellulose.

For example, the one or more pharmaceutically acceptable excipients further comprise a lubricant.

For example, the formulation comprises about 0.5 wt. % to about 5 wt. % lubricant, e.g., about 0.5 wt. %, 0.7 wt. %, 0.9 wt. %, 1 wt. %, 2 wt. %, 3 wt. %, 4 wt. %, or 5 wt. %.

For example, the lubricant is magnesium stearate.

For example, the one or more pharmaceutically acceptable excipients further comprise a coating composition.

For example, the formulation comprises about 1 wt. % to about 10 wt. % coating composition, e.g., about 1 wt. %, 2 wt. %, 3 wt. %, 4 wt. %, 5 wt. %, 6 wt. %, 7 wt. %, 8 wt. %, 9 wt. %, or 10 wt. %.

For example, the coating composition is a water-soluble, immediate-release coating composition.

For example, the coating composition comprises hypromellose.

For example, the coating composition further comprises talc and macrogol.

For example, the coating composition further comprises a colorant, e.g., titanium dioxide, iron (III) oxide, or both.

For example, the coating composition comprises one or more of polyvinyl alcohol, hypromellose, talc, and macrogol. For example, the coating composition further comprises titanium dioxide and/or iron (III) oxide. For example, the coating composition is Opadry 03F45063 RED.

For example, the formulation comprises an amount of the therapeutic agent equivalent to about 40-60 wt. % Compound 1, about 10-20 wt. % diluent, about 15-25 wt. % disintegrant, about 1-10 wt. % binder, about 0.5-5 wt. % lubricant, and about 1-10 wt. % coating composition. For example, the formulation comprises an amount of the therapeutic agent equivalent to about 40-60 wt. % Compound 1, about 12-18 wt. % diluent, about 18-23 wt. % disintegrant, about 2-6 wt. % binder, about 1-3 wt. % lubricant, and about 2-6 wt. % coating composition.

For example, the formulation consists of the therapeutic agent, lactose monohydrate, low-substituted hydroxypropyl cellulose, sodium starch glycolate, hydroxypropyl cellulose, and magnesium stearate. For example, the formulation consists of an amount of the therapeutic agent equivalent to about 35-65 wt. %, or 40-60 wt. %, or 45-55 wt. % of Compound 1, about 10-20 wt. % lactose monohydrate, about 11-19 wt. % low-substituted hydroxypropyl cellulose, about 3-7 wt. % sodium starch glycolate, about 1-10 wt. % hydroxypropyl cellulose, and about 0.5-5 wt. % magnesium stearate. For example, the formulation consists of an amount of the therapeutic agent equivalent to about 50 wt. % Compound 1, about 17 wt. % lactose monohydrate, about 15 wt. % low-substituted hydroxypropyl cellulose, about 5 wt. % sodium starch glycolate, about 4 wt. % hydroxypropyl cellulose, and about 2 wt. % magnesium stearate.

For example, the formulation consists of the therapeutic agent, lactose monohydrate, low-substituted hydroxypropyl cellulose, sodium starch glycolate, hydroxypropyl cellulose, magnesium stearate, and a coating composition. For example, the formulation consists of an amount of the therapeutic agent equivalent to about 40-60 wt. % Compound 1, about 10-20 wt. % lactose monohydrate, about 11-19 wt. % low-substituted hydroxypropyl cellulose, about 3-7 wt. % sodium starch glycolate, about 1-10 wt. % hydroxypropyl cellulose, about 0.5-5 wt. % magnesium stearate, and about 1-10 wt. % a coating composition. For example, the formulation consists of an amount of the therapeutic agent equivalent to about 47-48 wt. % Compound 1, about 16 wt. % lactose monohydrate, about 14-15 wt. % low-substituted hydroxypropyl cellulose, about 5 wt. % sodium starch glycolate, about 4 wt. % hydroxypropyl cellulose, about 2 wt. % magnesium stearate, and about 4 wt. % a coating composition.

For example, the formulation is an oral dosage formulation comprising an amount of the therapeutic agent equivalent to about 10 mg to about 1000 mg, or about 10 mg to about 800 mg, or about 10 mg to about 500 mg, or about 10 mg to about 400 mg of Compound 1 per unit dose. For example, the oral dosage formulation is in the form of a tablet. For example, the tablet comprises an amount of the therapeutic agent equivalent to about 25 mg to about 400 mg of Compound 1. For example, the tablet comprises an amount of the therapeutic agent equivalent to about 50 mg, about 75 mg, about 100 mg, about 125 mg, about 150 mg, about 175 mg, about 200 mg or about 400 mg of Compound 1.

For example, the formulation is a solid formulation. For example, the formulation is substantially free of water. In this context, "substantially" free of water means that the water content of the formulation at the time of packaging is less than 7%, less than 5%, less than 1%, or less than 0.5% of the total weight of the formulation. In one embodiment the amount of water is between 0.1 to 5% (e.g., 0.1-1% or 0.1-0.5%) of the total weight of the formulation. In one embodiment, the amount of water in the formulation of the invention manufactured through a spray-coating process is less than 0.5%.

The present invention relates to an oral formulation (e.g., in the form of a tablet) which is a stable formulation. For example, a stable formulation of the invention retains an amount of the active compound (e.g., Compound 1 or a salt thereof) in the formulation over a period of time (e.g., 3 months, 12 months, 18 months and 24 months), that is at least 90%, preferably at least 95%, and most preferably at least 99% the amount of the active compound initially present in the formulation. The storage condition can be 2-8 degrees Celsius (2-8° C.), or 25 degrees Celsius (25° C.) and 60% relative humidity, or 25° C. and 75% relative humidity, or 40° C. and 75% relative humidity.

The present invention relates to the pharmaceutical formulation comprising a therapeutic agent (e.g., Compound 1, or a salt thereof, or a combination thereof) and one or more pharmaceutically acceptable excipients selected from sodium starch glycolate, carmellose, carmellose calcium, croscarmellose sodium, or low-substituted hydroxypropylcellulose, and a combination thereof. In one embodiment, the excipients are selected from sodium starch glycolate, carmellose, carmellose calcium, or croscarmellose sodium, and a combination thereof. In one embodiment, the excipients are selected from sodium starch glycolate, or carmellose, and a combination thereof. In one embodiment, the pharmaceutical formulation further includes lactose, hydroxypropyl cellulose, or magnesium stearate or a combination thereof.

In one embodiment, the pharmaceutical formulation comprises an amount of the therapeutic agent equivalent to about 25-75 wt. % Compound 1, and about 5-35 wt. % excipients selected from sodium starch glycolate, carmellose, carmellose calcium, croscarmellose sodium, or low-substituted hydroxypropylcellulose, and a combination thereof. In one embodiment, the pharmaceutical formulation comprises an amount of the therapeutic agent equivalent to about 40-60 wt. % Compound 1, about 10-30 wt. % excipients selected from sodium starch glycolate, carmellose, carmellose calcium, croscarmellose sodium, or low-substituted hydroxypropylcellulose, and a combination thereof, about 10-20 wt. % diluent, about 2-6 wt. % binder, and about 1-3 wt. % lubricant.

In one embodiment, the pharmaceutical formulation comprises an amount of the therapeutic agent equivalent to about 50 wt. % Compound 1, about 20 wt. % excipients selected from sodium starch glycolate, carmellose, carmellose calcium, croscarmellose sodium, or low-substituted hydroxypropylcellulose, and a combination thereof, about 10-20 wt. % diluent, about 2-6 wt. % binder, and about 1-3 wt. % lubricant. In one embodiment, the formulation comprises an amount of the therapeutic agent equivalent to about 50 wt. % Compound 1, about 20 wt. % excipients selected from sodium starch glycolate, carmellose, and a combination thereof, about 10-20 wt. % lactose monohydrate, about 2-6 wt. % hydroxypropylcellulose, and about 1-3 wt. % magnesium stearate.

In one embodiment of the present invention, the composition of the formulation of the invention is provided in Table 3 in Example 2.

In one embodiment of the present invention, the composition of the formulation of the invention is provided in Tables 5-6 in Example 3, such as one of Formulation Nos. 1-5.

In one embodiment, the formulation is a solid formulation. In one embodiment, the formulation is in the form of a powder, granule, sachet, troche, or tablet. In one embodiment, the unit dose is a powder or tablet. In one embodiment, the tablet is in a blister pack or strip. For example, the blister pack or strip can be made of a material that is impermeable to water vapor and oxygen. In one embodiment, the blister pack is comprised of a metal foil. In one embodiment, the blister pack is a FOIL/FOIL blister pack. In one embodiment, the container of the blister pack is flushed with an inert gas such as nitrogen or argon. In one embodiment, the container further includes a desiccant such as a molecular sieve. In one embodiment, the unit dose is in a high density polyethylene bottle having a seal. In one embodiment, the bottle further comprises a desiccant. In one embodiment, the bottle further comprises an oxygen scavenger and/or a molecular sieve. In one embodiment, the bottle is substantially impermeable to oxygen and water vapor (e.g., much more impermeable than a HDPE bottle), such as an Oxy-Guard bottle.

The present invention also relates to a solid pharmaceutical composition comprising a therapeutic agent and means for achieving immediate release of the therapeutic agent, wherein the therapeutic agent is selected from Compound 1, a salt thereof, and a combination thereof.

For example, the means for achieving immediate release of the therapeutic agent allows release of at least 90%, or at least 80%, or at least 70%, or at least 60% of the therapeutic agent after 60 min. For example, the means for achieving immediate release of the therapeutic agent allows release of at least 90%, or at least 80%, or at least 70%, or at least 60% of the therapeutic agent after 45 min. For example, the means for achieving immediate release of the therapeutic agent allows release of at least 80%, or at least 70%, or at least 60% of the therapeutic agent after 30 min. For example, the means for achieving immediate release of the therapeutic agent allows an dissolution rate of at least about 90%, or at least about 80%, or at least about 70% in dissolution medium (pH 1.2, 900 mL, 37±0.5° C.) within 60, 45, or 30 minutes from the onset of dissolution study using the Apparatus 2 (Paddle Apparatus, paddle speed; 50 rpm) according to the procedure for immediate-release dosage form in 6.10 Dissolution test of JP 16 or <711> Dissolution of USP37. For example, the means for achieving immediate release of the therapeutic agent allows an dissolution rate of at least about 80%, or at least about 75%, or at least about 70%, or at least about 60% in dissolution medium (pH 4.5 acetate buffer, 900 mL, 37±0.5° C.) within 60, 45, or 30 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In another aspect, the present invention relates to a process of making the pharmaceutical formulation or composition disclosed herein. The process includes a) mixing a therapeutic agent, a diluent, a disintegrant and optionally a lubricant to form a first mixture, wherein the therapeutic agent is selected from the group consisting of Compound 1, a salt thereof, and a combination thereof. The process optionally includes one or more of the following steps:

b) adding an aqueous solution, or an organic solvent-based solution (e.g. IPA, EtOH, etc.), or an organic/aqueous mixture (e.g. 1:1 EtOH:Water) comprising a binder to the first mixture to form a second mixture;

c) granulating the second mixture to form wet granulates;

d) drying the wet granulates to form dried granulates;

e) size screening the dried granulates to obtain sized granulates;

f) mixing the sized granulates with a lubricant, and a second disintegrant to form a third mixture;

g) compressing the third mixture to form tablets; and h) applying a coating suspension to the tablets to generate film-coated tablets.

In certain embodiments, the present invention relates to a process of making the pharmaceutical formulation disclosed herein. The process includes a) mixing a therapeutic agent, a diluent, and a disintegrant to form a first mixture, wherein the therapeutic agent is selected from the group consisting of Compound 1, a salt thereof, and a combination thereof.

The process optionally includes one or more of the following steps:

b) granulating the first mixture to dry granulates;

e) size screening the dry granulates;

f) mixing the sized granulates with a lubricant, and a second disintegrant to form a third mixture;

g) compressing the third mixture to form tablets; and h) applying a coating suspension to the tablets to generate film-coated tablets.

The process of the invention can include one or more of the following features when applicable:

For example, the process does not include step e) size screening.

For example, the process does not include step h) coating.

For example, the process does not include step f) mixing with a lubricant and a second disintegrant.

For example, the process does not include step g) compressing.

For example, the diluent is lactose monohydrate,

For example, the disintegrant is low-substituted hydroxypropyl cellulose.

For example, the binder is hydroxypropyl cellulose.

For example, the lubricant is magnesium stearate.

For example, the second disintegrant comprises a low-substituted hydroxypropyl cellulose, sodium starch glycolate, or a combination thereof.

For example, the coating suspension comprises hypromellose. For example, the coating suspension further comprises water, talc, and/or macrogol. For example, the coating suspension further comprises one or more colorants.

In one embodiment of the present invention, the process of making the formulation of the invention is provided in FIG. 8. As shown in FIG. 8, the drug substance (e.g., Compound 1, its salt, or a combination thereof), lactose monohydrate and low-substituted hydroxypropyl cellulose are charged into a high shear mixer and mixed (Step 1: mixing). Then, hydroxypropyl cellulose is dissolved in purified water and then the solution is added to the mixer, and the mixture is granulated to produce wet granules (Step 2: granulation). The wet granules are then dried using a fluidized bed dryer to generate dried granules (Step 3: drying). Next, the dried granules are sized through a screen (Step 4: sizing). Then, the sized granules, low-substituted hydroxypropyl cellulose, sodium starch glycolate and magnesium stearate are blended together and lubricated in a tumble-type blender (Step 5: lubrication). The amount of low-substituted hydroxypropyl cellulose, sodium starch glycolate and magnesium stearate used for Step 5 is adjusted according to the yield of the sized granules. For example, the higher yield of the sized granules, higher amount of disintegrant and lubricant is used. Next, the lubricated granules are compressed into tablets using a tableting machine (Step 6: tableting). A coating suspension, which is prepared by mixing OPADRY 03F45063 RED with purified water, is then sprayed onto the tablets using a pan coating machine (Step 7: film-coating) to produce film-coated tablets.

In any method or formulation (e.g., an oral dosage form) described herein, in one embodiment, said cancer is advanced, refractory or resistant cancer. In any method or formulation (e.g., an oral dosage form) described herein, in one embodiment, said cancer is an INI1-deficient tumor.

In any method or formulation (e.g., an oral dosage form) described herein, in one embodiment, the subject is human.

In any method or formulation (e.g., an oral dosage form) described herein when applicable, the cancer is a solid tumor. Examples of the solid tumor described herein include, but are not limited to Colorectal adenocarcinoma, Cholangiocarcinoma, Pancreatic adenocarcinoma, Ewing's sarcoma, Synovial sarcoma, Alveolar sarcoma, Alveolar soft part sarcoma, Prostatic adenocarcinoma, Rhabdoid sarcoma, Malignant Rhabdoid tumor, and Urothelial carcinoma.

In any method or formulation (e.g., an oral dosage form) described herein when applicable, the cancer is a B cell lymphoma. Examples of the B cell lymphoma described herein include, but are not limited to Diffuse Large B-cell Lymphoma, Follicular Lymphoma, and Marginal Zone Lymphoma.

In any method or formulation (e.g., an oral dosage form) described herein when applicable, the cancer is a cancer with aberrant H3-K27 methylation.

In any method or formulation (e.g., an oral dosage form) described herein, the compound of Formula (I) or a pharmaceutically acceptable salt thereof is administered orally for at least 7, 14, 21, 28, 35, 42, 47, 56, or 64 days. In certain embodiments, the administration is a continuous administration without a drug holiday. For example, the compound of Formula (I) or a pharmaceutically acceptable salt thereof is administered orally, for 28 days in a 28-day cycle. In other embodiments, the compound is administered with a drug holiday. For example, the compound of Formula (I) or a pharmaceutically acceptable salt thereof is orally administered, e.g., for 21 days of a 28-day cycle with a 7-day drug holiday per cycle.

In any method or formulation (e.g., an oral dosage form) described herein, in certain embodiments, said single dose ranges from about 100 mg to about 1600 mg.

In any method or formulation (e.g., an oral dosage form) described herein, a single dose of the compound of Formula (I) or a pharmaceutically acceptable salt thereof is 100, 200, 400, 800 or 1600 mg.

In any method or formulation (e.g., an oral dosage form) described herein, in certain embodiments, said therapeutically effective amount is a single 400 mg dose, wherein said single dose provides a mean AUC(0-12) bioequivalent to a mean AUC(0-12) of from about 1720 ng*hr/ml to about 7798 ng*hr/ml, e.g., from about 1720 ng*hr/ml to about 3899 ng*hr/ml.

In any method or formulation (e.g., an oral dosage form) described herein, in certain embodiments, said therapeutically effective amount is a single 800 mg dose, wherein said single dose provides a mean AUC(0-12) bioequivalent to a mean AUC(0-12) of from about 7798 ng*hr/ml to about 9441 ng*hr/ml.

In any method or formulation (e.g., an oral dosage form) described herein, in certain embodiments, said therapeutically effective amount is a single 1600 mg dose, wherein said single dose provides a mean AUC(0-12) bioequivalent to a mean AUC(0-12) of from about 15596 ng*hr/ml to about 18882 ng*hr/ml.

In any method or formulation (e.g., an oral dosage form) described herein, in certain embodiments, said therapeutically effective amount is a single 400 mg dose, wherein said single dose provides a mean Cmax bioequivalent to a mean Cmax of from about 476 ng/ml to about 1730 ng/ml e.g., from about 476 ng/ml to about 865 ng/ml.

In any method or formulation (e.g., an oral dosage form) described herein, in certain embodiments, said therapeutically effective amount is a single 800 mg dose, wherein said single dose provides a mean Cmax bioequivalent to a mean Cmax of from about 1730 ng/ml to about 2063 ng/ml.

In any method or formulation (e.g., an oral dosage form) described herein, in certain embodiments, said therapeutically effective amount is a single 1600 mg dose, wherein said single dose provides a mean Cmax bioequivalent to a mean Cmax of from about 3460 ng/ml to about 4125 ng/ml.

In any method or formulation (e.g., an oral dosage form) described herein, in certain embodiments, said administering comprises administering orally a dosage form to the subject, twice per day or three times per day.

In any method or formulation (e.g., an oral dosage form) described herein, in certain embodiments, said single dose provides a median Tmax of from about 1 hour to about 2 hours.

In any method or formulation (e.g., an oral dosage form) described herein, in certain embodiments, said oral dosage form or formulation comprises an amount of therapeutic agent equivalent to about 25 mg to about 400 mg (e.g., equivalent to about 25 mg to about 200 mg) of EPZ-6438 per unit dose.

In any method or formulation (e.g., an oral dosage form) described herein, in certain embodiments, said oral dosage form or formulation provides an dissolution rate of at least about 90%, or at least about 80%, or at least about 70% in dissolution medium (pH 1.2, 37±0.5° C.) within 60 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In any method or formulation (e.g., an oral dosage form) described herein, in certain embodiments, said oral dosage form or formulation provides an dissolution rate of at least about 90%, or at least about 80%, or at least about 70% in dissolution medium (pH 1.2, 37±0.5° C.) within 45 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In any method or formulation (e.g., an oral dosage form) described herein, in certain embodiments, said oral dosage form or formulation provides an dissolution rate of at least about 90%, or at least about 80%, or at least about 70% in dissolution medium (pH 1.2, 37±0.5° C.) within 30 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In any method or formulation (e.g., an oral dosage form) described herein, in certain embodiments, said oral dosage form or formulation provides an dissolution rate of at least about 80%, or at least about 75%, or at least about 70%, or at least about 60% in dissolution medium (pH 4.5 acetate buffer, 37±0.5° C.) within 60 minutes from the onset of dissolution study using the Apparatus 2 (Paddle Apparatus, paddle speed; 50 rpm) according to the procedure for immediate-release dosage form in 6.10 Dissolution test of JP 16 or <711> Dissolution of USP37.

In any method or formulation (e.g., an oral dosage form) described herein, in certain embodiments, said oral dosage form or formulation comprises sodium starch glycolate or carmellose or a combination thereof as pharmaceutically acceptable carrier or excipient.

Other compounds suitable for the methods of the invention are described in U.S. Publication 20120264734, the contents of which are hereby incorporated by reference in their entireties. Further, Compound 1 is suitable for administration as part of a combination therapy with one or more other therapeutic agents or treatment modality, suitable to be administered together, sequentially, or in alternation.

In one embodiment, Compound 1 or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating cancer (e.g., a solid tumor, B cell lymphoma or a cancer with aberrant H3-K27 methylation).

In one embodiment, Compound 1 or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating an INI1-deficient tumor.

In one embodiment, Compound 1 or a pharmaceutically acceptable salt thereof is administered in combination (either simultaneously or sequentially) with a standard of care agent, such as one or more components of R-CHOP, a BCL inhibitor, or a BCR inhibitor. For example, Compound 1 (or EPZ-6438) or a pharmaceutically acceptable salt thereof has either additive or synergistic effects when combined with drugs that target the BCR/PI3K pathways in cell lines harboring either mutant EZH2, or WT EZH2 germinal center lymphoma cell lines. There has been no effect observed in ABC lymphoma cell lines when they are exposed to a combination of EPZ-6438 and drugs that target BCR/PI3K pathways. Importantly, EPZ-6438, combined with a drug that targets the BCR/PI3K pathways, shows a synergistic effect in germinal center B-cell lymphoma (GCB lymphoma) cell lines, regardless of whether the GCB-lymphoma cell lines contained WT or mutant EZH2 protein.

Other embodiments or examples of combination therapy are described in a co-pending application, i.e., International Application No. PCT/US2014/069167, which claims priority to and the benefit of U.S. Ser. No. 61/913,063 filed Dec. 6, 2013, U.S. Ser. No. 61/934,338 filed Jan. 31, 2014, and U.S. Ser. No. 61/992,881 filed May 13, 2014, the contents of each of which are hereby incorporated by reference in their entireties.

In one embodiment, the compound of the invention is the compound itself, i.e., the free base or "naked" molecule. In another embodiment, the compound is a salt thereof, e.g., a mono-HCl or tri-HCl salt, mono-HBr or tri-HBr salt of the naked molecule.

The use of the articles "a", "an", and "the" herein are to be construed to cover both the singular and the plural, unless otherwise indicated herein or clearly contradicted by context. For example, the term "a disintegrant" refers to one or more disintegrants included in or suitable for use in the formulation described herein. Similarly, the term "a therapeutic agent" refers to one or more therapeutic agents included in or suitable for use in the formulation described herein. For example, the formulation described herein can include Compound 1 alone as the therapeutic agent or active ingredient or include a mixture of Compound 1 and another compound (e.g., HBr salt of Compound 1 or another anti-cancer drug). The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

The concentration of the therapeutic agent in the formulation is expressed as equivalent to a certain amount of Compound 1. As used herein, the term "equivalent" amount or weight percentage refers to the quantity of the drug substance that is adjusted as per potency adjustment factor, a value derived for the assay value obtained from Compound 1. Methods for determining the equivalent amount are well known in the art (see, e.g., http://www.fda.gov/downloads/Drugs/.../Guidances/ucm070246.pdf).

The term "about", "approximately", or "approximate", when used in connection with a numerical value, means that a collection or ranger of values is included. For example, "about X" includes a range of values that are ±10%, ±5%, ±2%, ±1%, ±0.5%, ±0.2%, or ±0.1% of X, where X is a numerical value. In addition, "about X" may also include a range of X±0.5, X±0.4, X±0.3, X±0.2, or X±0.1, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. An example of keto-enol equilibria is between pyridin-2(1H)-ones and the corresponding pyridin-2-ols, as shown below.

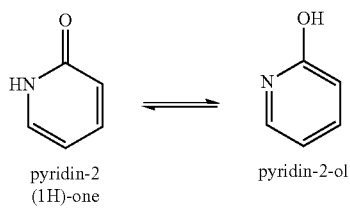 [SMILES: O=c1cccc[nH]1 ; Oc1ccccn1]

pyridin-2(1H)-one     pyridin-2-ol

It is to be understood that the compounds used in the formulation of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystalline forms" means crystal structures in which a compound (or a salt or solvate thereof) can crystallize in different crystal packing arrangements, all of which have the same elemental composition. Different crystal forms usually have different XRPD patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

The compounds of the invention include the compounds themselves, as well as their N-oxides, salts, their solvates, and their prodrugs, if applicable. A salt, for example, can be formed between an anion and a positively charged group (e.g., amino) on a substituted purine or 7-deazapurine compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a substituted purine or 7-deazapurine compound. Suitable cations include sodium ion, potassium ion, magnesium ion, calcium ion, and an ammonium cation such as tetramethyl-ammonium ion. The substituted purine or 7-deazapurine compounds also include those salts containing quaternary nitrogen atoms. Examples of prodrugs include esters and other pharmaceutically acceptable derivatives, which, upon administration to a subject, are capable of providing active substituted purine or 7-deazapurine compounds.

Additionally, the compounds or crystalline forms of the present invention, for example, the salts of the compounds or crystalline forms, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof has an INI1-deficient tumor.

INI1 is a regulatory complex that opposes the enzymatic function of EZH2. Due to a variety of genetic alterations, INI1 loses its regulatory function. As a result, EZH2 activity is misregulated, causing EZH2 to play a driving, oncogenic role in a set of genetically defined cancers that include synovial sarcomas and malignant rhabdoid tumors.

Synovial sarcoma is a malignant tumor of the soft tissues and is one of the most common soft tissue tumors in adolescents and young patients. Mean age of patients at diagnosis is approximately 30 years Malignant rhabdoid tumors, or MRT, are a rare and deadly form of childhood cancer that is caused by a specific genetic alteration that leads to misregulated EZH2 function. MRT typically presents either in the kidney or brain and in children less than two years of age.

A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, prodrug, metabolite, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

The methods and uses described herein may include steps of detecting the presence or absence of one or more EZH2 mutations in a sample from a subject in need thereof prior to and/or after the administration of a compound or composition described herein to the subject. By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

Point mutations of the EZH2 gene at a single amino acid residue (e.g., Y641, A677, and A687) of EZH2 have been reported to be linked to lymphoma. More examples of EZH2 mutants and methods of detection of mutation and methods treatment of mutation-associated disorders are described in, e.g., U.S. Patent Application Publication No. US 20130040906, the entire content of which is incorporated herein by reference in its entirety.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

The present invention also provides pharmaceutical compositions comprising one or more active compounds (e.g., Compound 1 or a salt thereof) in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The term "unit dosage form" as used herein refers to physically discrete units suited as unitary dosages for the subject to be treated; each unit containing a predetermined quantity of active compound calculated to produce the desired therapeutic effect in association with the required pharmaceutical carrier. The unit dosage form is any of a variety of forms, including, for example, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

In one embodiment, the unit dosage form is an oral dosage form. In one embodiment, the unit dosage form is a tablet.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. For example, a pharmaceutically acceptable excipient used for the formulation of the invention can be a diluent or inert carrier, a lubricant, a binder, or a combination thereof. The pharmaceutically acceptable excipient used for the formulation of the invention can further include a filler, an anti-microbial agent, an antioxidant, an anti-caking agent, a coating agent, or a mixture thereof.

Examples of pharmaceutically acceptable excipients include, but are not limited to binders, fillers, disintegrants, lubricants, anti-microbial agents, antioxidant, and coating agents.

Exemplary binders include, but are not limited to corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc.), methyl cellulose, Methocel, pre-gelatinized starch (e.g., STARCH 1500® and STARCH 1500 LM®, sold by Colorcon, Ltd.), hydroxypropyl cellulose, hydroxypropyl methyl cellulose, microcrystalline cellulose (FMC Corporation, Marcus Hook, Pa., USA), Emdex, Plasdone, or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof.

Exemplary disintegrants include, but are not limited to: agar-agar, alginic acid, calcium carbonate, microcrystalline cellulose, croscarmellose sodium, crospovidone, polacrilin potassium, sodium starch glycolate (such as Explotab), potato or tapioca starch, other starches, pre-gelatinized starch, clays, other algins, other celluloses, gums (like gellan), low-substituted hydroxypropyl cellulose, ployplasdone, or mixtures thereof.

Exemplary lubricants include, but are not limited to: calcium stearate, magnesium stearate, mineral oil, light mineral oil, glycerin, sorbitol, mannitol, polyethylene glycol, other glycols, compritol, stearic acid, sodium lauryl sulfate, sodium stearyl fumarate (such as Pruv), vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Deaussa Co., Piano, Tex. USA), a pyrogenic silicon dioxide (CAB-O-SIL, Cabot Co., Boston, Mass. USA), or mixtures thereof.

Exemplary anti-caking agents include, but are not limited to: calcium silicate, magnesium silicate, silicon dioxide, colloidal silicon dioxide, talc, or mixtures thereof.

Exemplary antimicrobial agents include, but are not limited to: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof.

Exemplary antioxidants include, but are not limited to: ascorbic acid, BHA, BHT, EDTA, or mixture thereof.

Exemplary coating agents include, but are not limited to: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, carnauba wax, microcrystalline wax, gellan gum, maltodextrin, methacrylates, microcrystalline cellulose and carrageenan or mixtures thereof.

The formulation described herein can also include other excipients and categories thereof including but not limited to Pluronic®, Poloxamers (such as Lutrol® and Poloxamer 188), ascorbic acid, glutathione, protease inhibitors (e.g. soybean trypsin inhibitor, organic acids), pH lowering agents, creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, mannitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In certain embodiments, the formulation of the invention is a solid oral dosage form that may optionally be treated with coating systems (e.g. Opadry® fx film coating system) to be coated with for example Opadry® blue (OY-LS-20921), Opadry® white (YS-2-7063), Opadry® white (YS-1-7040), and black ink (S-1-8 106).

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

The pharmaceutical compositions of the present invention containing active compounds may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds in the formulation of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

Unless specifically stated or obvious from context, as used herein, the term "or" is understood to be inclusive.

Unless otherwise clear from the context, all numerical values provided herein are modified by the term "about."

The list of the abbreviations used in this disclosure and Figures is presented as follows.

AE: adverse event

AUC: Area under the plasma concentration-time curve

AUC(0-x): Area under the plasma concentration-time curve from time zero to x hours after dosing AUC(0-t): Area under the plasma concentration-time curve from time zero to time of last quantifiable concentration AUC(0-inf): Area under the plasma concentration-time curve from time zero to infinity ANCOVA: Analysis of covariance
BID: twice a day
CI: Confidence interval
Cmax: Maximum drug concentration
Cx: plasma concentration at x hours after dosing
CV: Coefficient of variation
DLT: dose-limiting toxicity
MTD: Maximum tolerated dose
PO: orally
PD: Pharmacodynamics
PK: Pharmacokinetic(s)
T½: Terminal elimination half-life
Tmax: Time to reach maximum (peak) concentration following drug administration

EXAMPLE

Example 1 PK/PD STUDY

Phase 1 first-in-human study was conducted using the enhancer of zeste-homolog 2 (EZH2) histone methyl transferase inhibitor EPZ-6438 as a single agent in patients with advanced solid tumors ("ST") or B cell lymphoma.

Phase 1 dose escalation is being performed to determine maximum tolerated dose (MTD) safety, PK, PD, and preliminary anti-tumor activity in patients ("pts") with B cell lymphoma or advanced solid tumors.

Methods:

EPZ-6438 was administered PO BID continuously to cohorts of 3 to 6 pts up to a maximum feasible dose of 1600 mg BID. Blood samples for PK and skin biopsies for PD analysis were collected. PD samples were stained with H3K27me3 specific antibody and percent change from baseline in H3K27Me3 positive cells was determined. PK/PD relationship was analyzed. Tumor assessments were performed every 8 weeks.

As of 14 Aug. 2014, 21 patients have been enrolled and treated at 5 dose levels of 100, 200, 400, 800, and 1600 mg BID. Diagnoses for B cell NHL included follicular lymphoma (FL, n=4), DLBCL (n=4, including 1 patient ("pt") with primary mediastinal lymphoma [PMBL] and marginal zone lymphoma (n=1)). ST pts included 1 pt with MRT. 11 pts (7 ST, 4 B-cell NHL) had at least 1 documented post-treatment assessment and are evaluable for efficacy. Median age was 59 yrs (range 23-83). 1 DLT of thrombocytopenia has been reported at 1600 mg BID. Frequently occurring AEs independent of causality were asthenia (8 pts), anaemia (4 pts), decreased appetite and diarrhoea (3 pts each), pulmonary embolism, insomnia, muscle spasms, thrombocytopenia, nausea, and vomiting (2 pts each). 5/21 pts experienced Grade 3/4 AE. EPZ-6438 PK exhibit rapid absorption (Tmax=1-2 hrs), dose related increase in exposure and rapid elimination (half-life~4 hr). Lower EPZ-6438 exposure on multiple dosing was associated with higher metabolite exposure. There was an exposure-related decrease in H3K27Me3 positive cells in skin. Partial responses were demonstrated in 2 of 4 evaluable NHL pts (1 transformed DLBCL, 100 mg BID, and 1 PMBL, 200 mg BID) and in 1 pt with MRT with INI1 deficiency (800 mg BID). Further cohort expansion is ongoing.

The study showed that EPZ-6438 is well tolerated up to 1600 mg BID with preliminary evidence of activity in NHL and MRT and exposure related inhibition of H3K27Me3. MTD has not been reached. These data support continuing development of EPZ-6438 in B cell lymphoma and INI1-deficient tumors in Phase 2 studies.

Pharmacokinetics

Figure 1B:
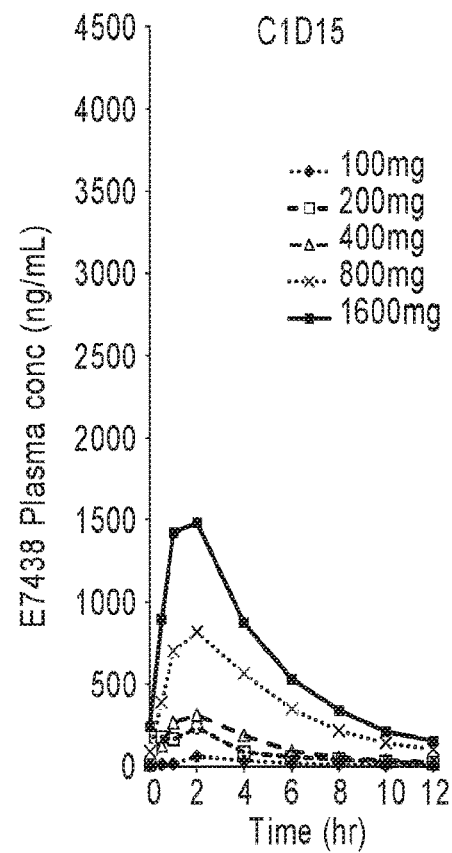

Pharmacokinetics of EPZ-6438 and its major desethyl metabolite, ER-897387, were characterized following single (Day 1) and multiple (Day 15) administration to subjects with advanced solid tumors or B-cell lymphoma in Dose-Escalation Study. Doses administered were 100 mg BID as a suspension (n=3) or tablet (n=3) formulation and 200, 400, 800 and 1600 mg as tablet formulation. On Day 1, EPZ-6438 was rapidly absorbed with maximum plasma EPZ-6438 concentration observed approximately 1 to 2 hours post dose (Table 1). Plasma concentrations declined in a bi-exponential manner with quantifiable levels of both EPZ-6438 and its metabolite, ER-897387 measurable up to 12 hours post dose (FIG. 1). The mean EPZ-6438 terminal half-life ($t_{1/2}$) was approximately 3 to 6 hours. EPZ-6438 exposure was slightly higher than dose-proportional, highly variable (% CV=32%-95%) and comparable between the tablet and suspension formulations. EPZ-6438 conversion to ER-897387 ranged from approximately 39% to 104% and 58% to 156% with respect to Cmax and $AUC_{(0\text{-}12\ h)}$ on Day 1, respectively.

After multiple dosing (Day 15), the median time to reach maximum plasma concentrations ($t_{max}$) was 1 to 2 hours. The terminal half-life remained unchanged on Day 15 ($t_{1/2}$=approximately 3-6 hours) across the dose range. After multiple dosing, there was a dose-dependent decrease in EPZ-6438 exposure. The EPZ-6438 accumulation ratio ($R=AUC_{D15}/AUC_{D1}$) was approximately 74% and 44% following 100 mg and 1600 mg dose administration, respectively.

Figure 2:
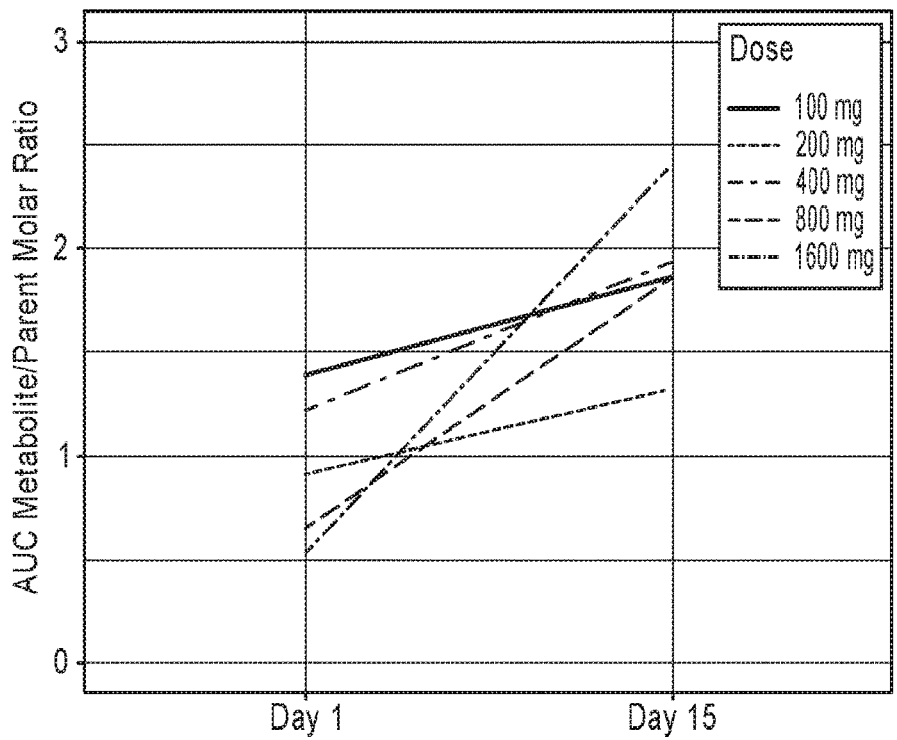
FIG. 2 is a plot of mean metabolite-to-parent (ER-897387/EPZ-6438) exposure molar ratio following a single dose (Day 1) and multiple doses (Day 15) twice-daily dosing.

Maximum ER-897387 concentrations were observed at 0.5 to 2 hours post dose and its elimination paralleled that of EPZ-6438 ($t_{1/2}$=3-6 hours). The amount of metabolite formed increased after multiple dosing (FIG. 2). The increase in ER-897387 exposure on Day 15 correlated with the decrease in EPZ-6438 exposure, indicating metabolism induction.

TABLE 1

Mean (Standard Deviation) Pharmacokinetic Parameters for EPZ-6438 and ER-897387 Following Single (Day 1) Twice-Daily Administration of EPZ-6438

| | | E7438 | | | | | | ER-897387 | | | |
|---|---|---|---|---|---|---|---|---|---|---|---|
| | | | | | $C_{max}$ | | $AUC_{0\text{-}12\ hr}$ | | | | |
| Dose (mg) | n | $t_{1/2}$ (hr) | $T_{max}$# (hr) | $C_{max}$ (ng/mL) | per 1 mg (ng/mL) | $AUC_{0\text{-}12\ hr}$ (hr*ng/mL) | per 1 mg (hr*ng/mL) | $t_{1/2}$ (hr) | $T_{max}$# (hr) | $C_{max}$ (ng/mL) | $AUC_{0\text{-}12\ hr}$ (hr*ng/mL) |
| 100 (S) | 3 | 4.14 (0.803) | 0.50 (0.50-1.0) | 169 (136) | 1.7 | 467 (446) | 4.7 | 4.72 (0.350) | 0.50 (0.50-1.0) | 93.9 (1.46) | 326 (21.5) |
| 100 (T) | 3 | 2.73 (0.275) | 1.0 (1.0-2.0) | 102 (80.0) | 1.0 | 337 (247) | 3.4 | 3.00 (0.422) | 2.0 (1.0-2.0) | 102 (37.5) | 447 (176) |

TABLE 1-continued

Mean (Standard Deviation) Pharmacokinetic Parameters for EPZ-6438 and ER-897387 Following Single (Day 1) Twice-Daily Administration of EPZ-6438

| | | E7438 | | | | | | ER-897387 | | | |
|---|---|---|---|---|---|---|---|---|---|---|---|
| | | | | | | $C_{max}$ | $AUC_{0-12\,hr}$ | | | | |
| Dose (mg) | n | $t_{1/2}$ (hr) | $T_{max}^{\#}$ (hr) | $C_{max}$ (ng/mL) | per 1 mg (ng/mL) | $AUC_{0-12\,hr}$ (hr*ng/mL) | per 1 mg (hr*ng/mL) | $t_{1/2}$ (hr) | $T_{max}^{\#}$ (hr) | $C_{max}$ (ng/mL) | $AUC_{0-12\,hr}$ (hr*ng/mL) |
| 200 | 3 | 3.42 (0.631) | 1.0 (0.50-1.0) | 363 (155) | 1.8 | 1247 (623) | 6.2 | 3.23 (0.655) | 1.0 (1.0-1.0) | 267 (47.8) | 1077 (224) |
| 400 | 3 | 2.88 (0.294) | 2.0 (2.0-4.0) | 476 (258) | 1.2 | 1720 (550) | 4.3 | 3.75 (0.714) | 2.0 (2.0-4.0) | 384 (80.9) | 2003 (595) |
| 800 | 6 | 3.81 (0.92) | 2.0 (1.0-2.0) | 1730 (564) | 2.2 | 7798 (3357) | 9.7 | 5.36 (1.54) | 2.0 (2.0-2.0) | 793 (222) | 4854 (908) |
| 1600 | 6* | 3.67 (1.09) | 2.0 (1.0-2.0) | 4125 (1925) | 2.6 | 18882 (6387) | 11.8 | 6.1 (1.10) | 2.0 (2.0-8.0) | 1318 (516) | 9465 (2986) |

*n = 5 for $t_{1/2}$
statistic for Tmax is expressed as Median with Min-Max range

TABLE 2

Mean (Standard Deviation) Pharmacokinetic Parameters for EPZ-6438 and ER-897387 Following Multiple Dose (Day 15) Twice-Daily Administration of EPZ-6438

| | | EPZ-6438 | | | | ER-897387 | | | |
|---|---|---|---|---|---|---|---|---|---|
| Dose (mg) | $^a$n | $C_{max}$ (ng/mL) | $^b t_{max}$ (hr) | $AUC_{(0-12\,h)}$ (ng·h/mL) | $t_{1/2}$ (hr) | $C_{max}$ (ng/mL) | $^b t_{max}$ (hrs) | $AUC_{(0-12\,h)}$ (ng·h/mL) | $t_{1/2}$ (hr) |
| 100 (S) | 3 | 156 (174) | 1.0 (0.50-2.0) | 416 (380) | 5.65 (0.756) | 123 (18.8) | 1.0 (0.5-2.0) | 445 (15.5) | 4.92 (0.387) |
| 100 (T) | 3 | 62.2 (60.8) | 2.0 (1.0-2.0) | 252 (183) | 3.20 (1.09) | 81.4 (38.1) | 2.0 (1.0-2.0) | 446 (164) | 4.06 (1.60) |
| 200 (T) | 3 | 355 (154) | 1.0 (0.5-2.0) | 976 (375) | 3.82 (1.75) | 358 (199) | 2.0 (1.0-2.0) | 1227 (686) | 3.92 (1.49) |
| 400 (T) | 3 | 416 (99.9) | 1.0 (1.0-2.0) | 1475 (797) | 3.05 (0.0709) | 574 (211) | 2.0 (1.0-4.0) | 2723 (641) | 4.25 (0.459) |
| 800 (T) | 6 | 957 (396) | 1.0 (1.0-4.0) | 4553 (1636) | 4.08 (0.936) | 1288 (352) | 3.0 (2.0-4.0) | 8050 (1896) | 4.05 (0.776) |
| 1600 (T) | 6 | 2007 (1038) | 2.0 (1.0-4.0) | 7667 (3065) | 3.42 (0.479) | 2787 (322) | 2.0 (2.0-2.0) | 17580 (2098) | 4.47 (0.893) |

Pharmacodynamics

Figure 3A:
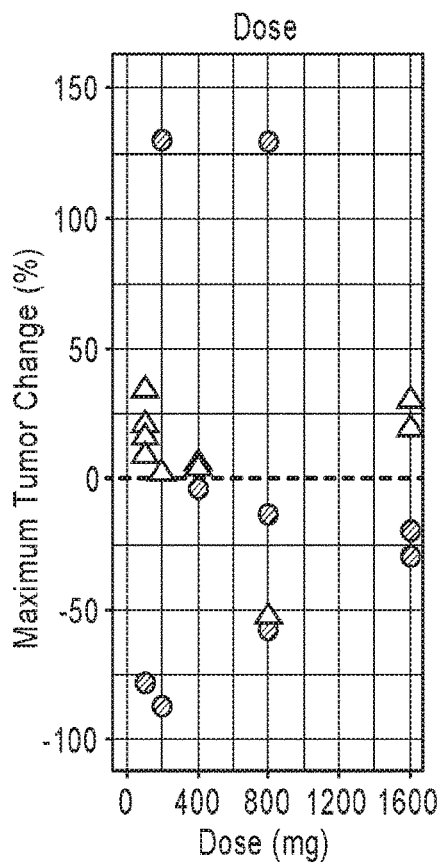
FIG. 3A is a plot of maximum tumor change vs dose and vs
Figure 3B:
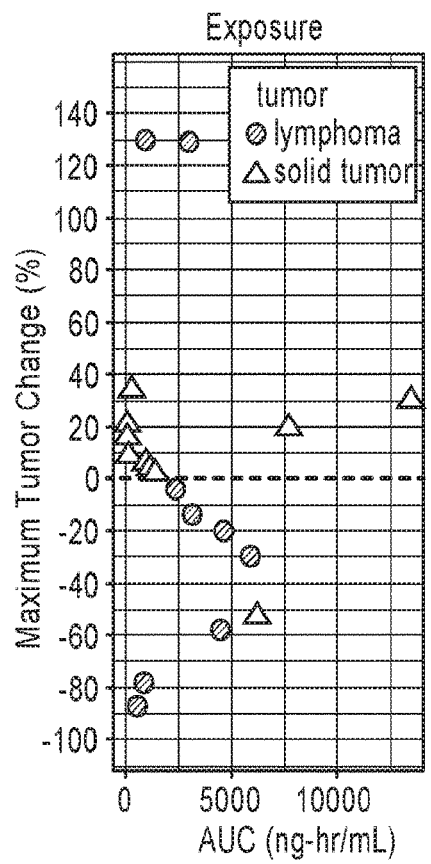
FIG. 3B is a plot of maximum tumor change vs steady-state (Day 15) exposure.

There was no direct correlation between percent maximum tumor change and EPZ-6438 dose (FIG. 3). Maximum tumor changes −78% and −87% were observed in 100 mg and 200 mg dose group, respectively. Higher EPZ-6438 exposure was not associated with greater tumor reduction.

Figure 4:
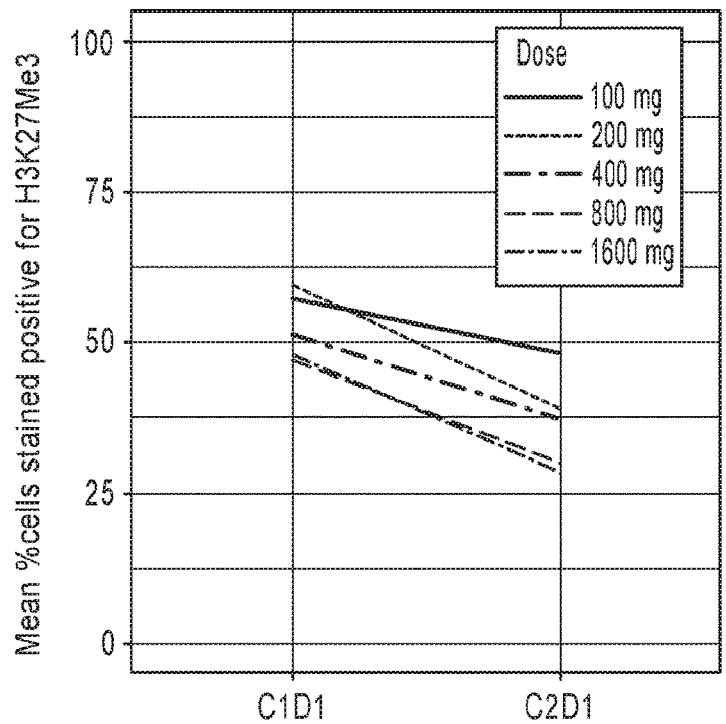
FIG. 4 is a diagram showing mean percent cells stained positive for H3K27Me3 in skin biopsy samples (C1D1=Cycle 1, Day 1 predose baseline; C2D1=Cycle 2, Day 1).
Figure 5:
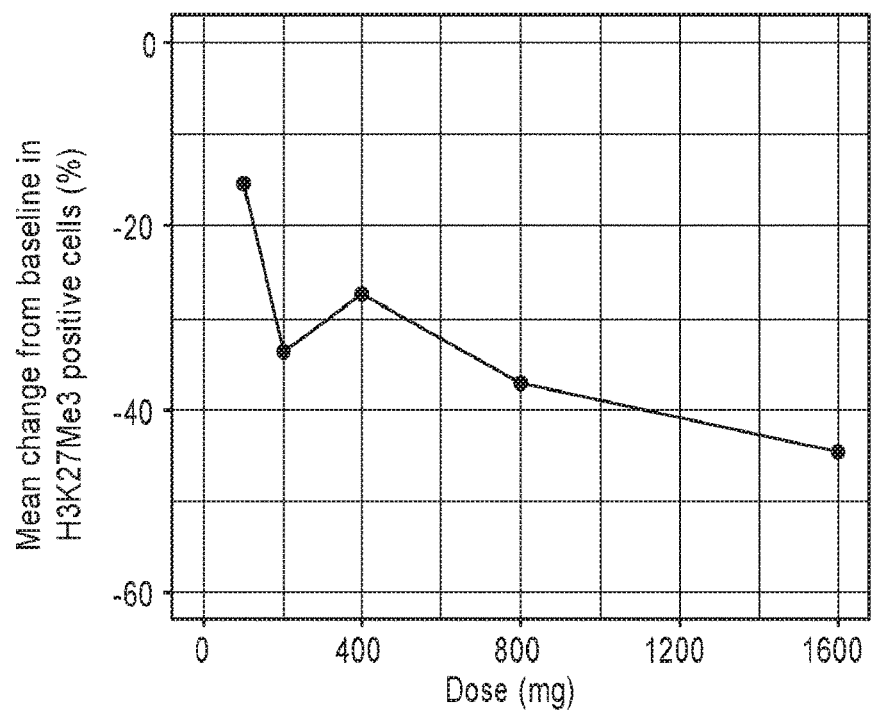
FIG. 5 is a plot of percent change from baseline in cells stained positive for H3K27Me3 in skin biopsy vs EPZ-6438 dose.
Figure 6:
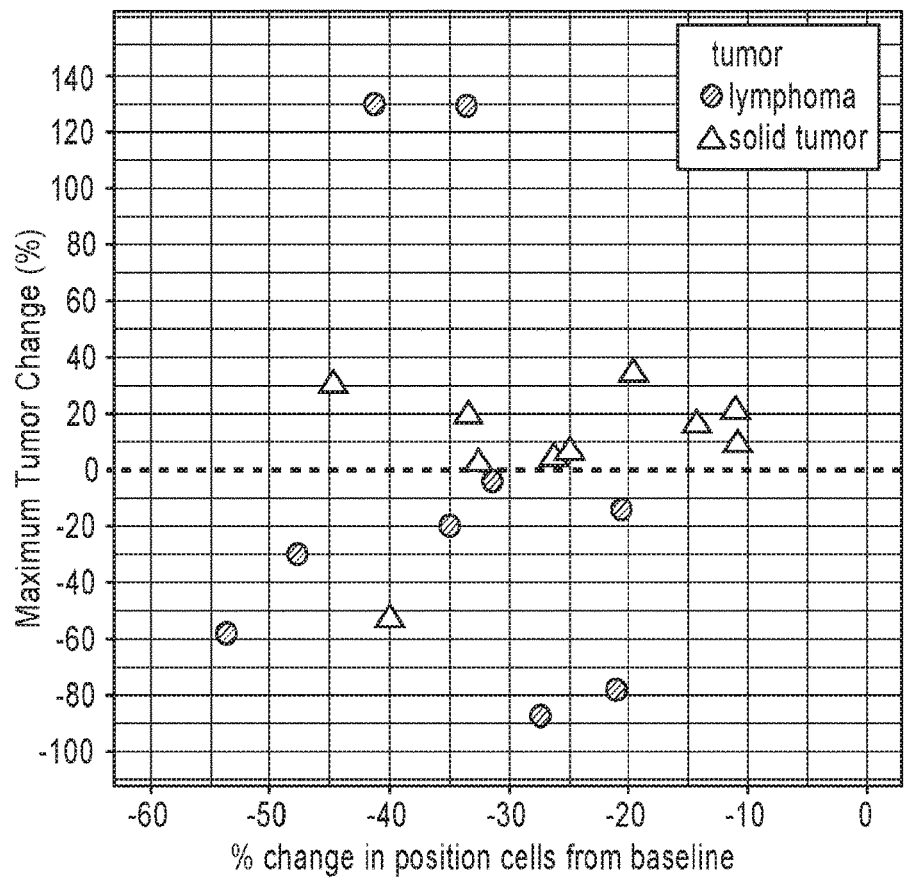
FIG. 6 is a plot of maximum percent tumor change vs percent change from baseline in cells stained positive for H3K27Me3 in skin biopsy.

Skin biopsies were collected predose (Cycle 1, Day 1) and predose prior to Cycle 2, Day 1 for immunohistochemistry analysis. Skin samples were stained with H3K27Me3 specific antibody and percent change from baseline in H3K27Me3 positive cells in the epidermis was determined. There was a consistent decrease in the number of cells stained positive for H3K27Me3 on Cycle 2, Day1 of EPZ-6438 dosing, confirming inhibition of histone H3 lysine 27 trimethylation in the skin (FIG. 4. The effect was dose dependent (FIG. 5 and did not correlate with maximum change in tumor (FIG. 6).

Figure 7:
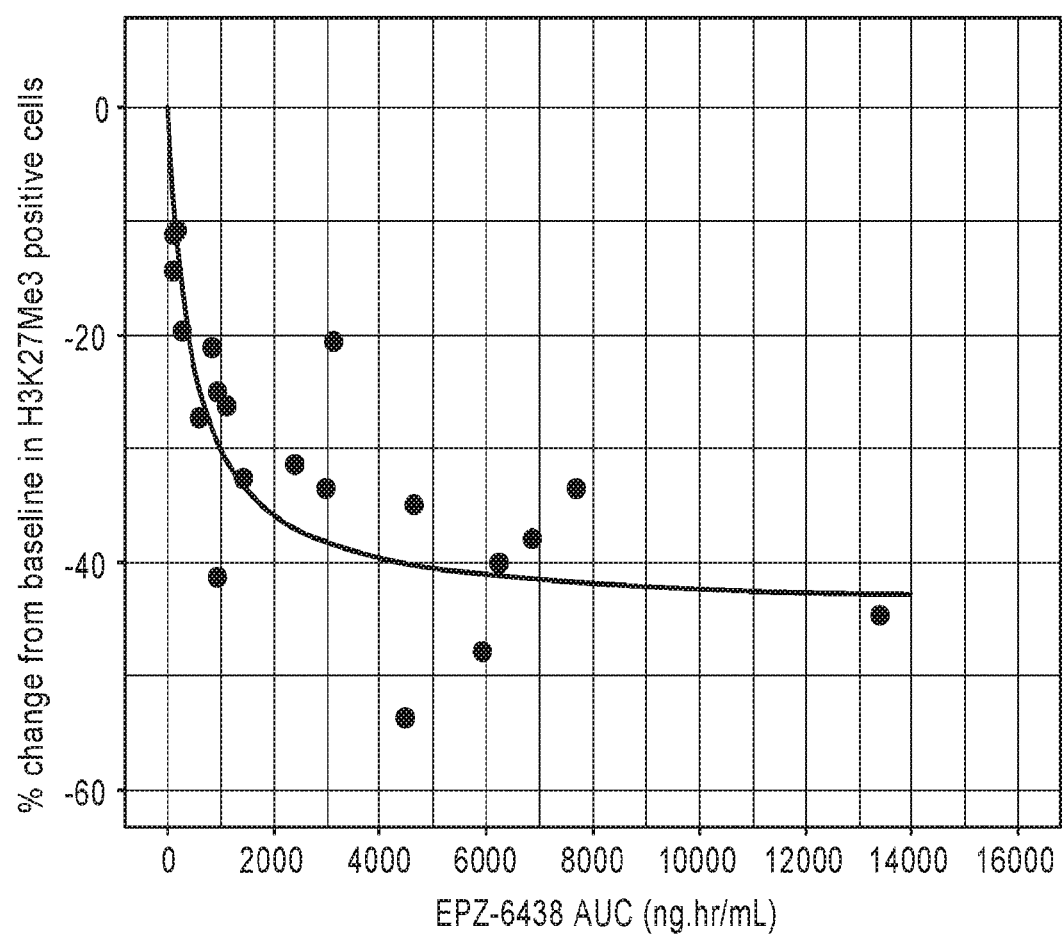
FIG. 7 is a plot showing correlation between percent change from baseline in cells stained positive for H3K27Me3 in skin biopsy samples and EPZ-6438 exposure. (Line represents a fit to an inhibitory PK/PD model).

A decrease in histone H3 lysine 27 trimethylation correlated with EPZ-6438 exposure (FIG. 7). An inhibitory Emax PK/PD model was fit to describe this relationship.

$$E = E_0 - \frac{I_{max} * AUC}{IC_{50} + AUC}$$

The model was parameterized in terms of maximal inhibition (Imax) and exposure associated with 50% of maximal inhibition (IC50). The model estimated Imax=−44.4% and IC50=487 ng.hr/mL. Model predicted EPZ-6438 exposure associated with 90% of maximal inhibition (IC90) is 4421 ng*hr/mL. This estimate is comparable to EPZ-6438 exposure sustained following 800 mg dose administration (mean Day 15 AUC=4553 ng*hr/mL).

The results indicate that:

EPZ-6438 is rapidly absorbed and eliminated (t½~3-6 hr)

EPZ-6438 exposure is greater than dose proportional and highly variable (% CV=32%-95%)

EPZ-6438 is extensively metabolized (AUC Metabolite/Parent=58-156%)

Substantial decrease in EPZ-6438 exposure on multiple dosing is associated with increase in metabolite formation No direct correlation was observed between maximum reduction in tumor size and EPZ-6438 or exposure. Greatest reduction in tumor size was observed at lowest doses (100 and 200 mg)

There was a correlation between biological activity in skin and EPZ-6438 exposure.

Model predicted exposure that result in near maximal inhibition (90%) is observed at EPZ-6438 exposure sustained at 800 mg dose Example 2 Film-Coated Tablets Formulations of EPZ-6438 were prepared according to methods disclosed herein. Table 3 below provides components and amounts thereof for the 50 mg, 100 mg, and 200 mg strength tablets:

TABLE 3

Components and Compositions of EPZ-6438 Film-coated Tablets

| Component | Composition | | | Specification |
|---|---|---|---|---|
| | 50 mg mg | 100 mg mg | 200 mg mg | |
| Core Tablet (Internal Phase) | | | | |
| EPZ-6438 Drug Substance [a] (equivalent to free form) | 57.1 (50.0) | 114.1 (100.0) | 228.3 (200.0) | In-house |
| Lactose Monohydrate [b] | 17.0 | 34.1 | 68.1 | NF |
| Low-substituted Hydroxypropyl Cellulose | 10.0 | 20.0 | 40.0 | NF |
| Hydroxypropyl Cellulose | 4.0 | 8.0 | 16.0 | NF |
| Purified Water [c] | q.s. | q.s. | q.s. | USP |
| (External Phase) | | | | |
| Low-substituted Hydroxypropyl Cellulose [d] | 5.0 | 10.0 | 20.0 | NF |
| Sodium Starch Glycolate (Type A) [d] | 5.0 | 10.0 | 20.0 | NF |
| Magnesium Stearate [d] | 1.9 | 3.8 | 7.6 | NF |
| Sub-total | 100.0 | 200.0 | 400.0 | — |
| Film-coat | | | | |
| Opadry 03F45063 RED | 4.5 | 8.0 | 12.5 | In house |
| Purified Water [c] | q.s. | q.s. | q.s. | USP |
| Total Weight | 104.5 | 208.0 | 412.5 | — |

NF = National Formulary (US), USP = United States Pharmacopeia, q.s. = quantum sufficit.
[a] The quantity of EPZ-6438 drug substance is adjusted as per potency adjustment factor, a derived value for the assay value in free form.
[b] Compounding amount of lactose monohydrate is adjusted depending on the quantity of EPZ-6438 drug substance in order to maintain constant weight of core tablets.
[c] Removed during drying process.
[d] Adjusted according to the yield of sized granules.

Figure 9:
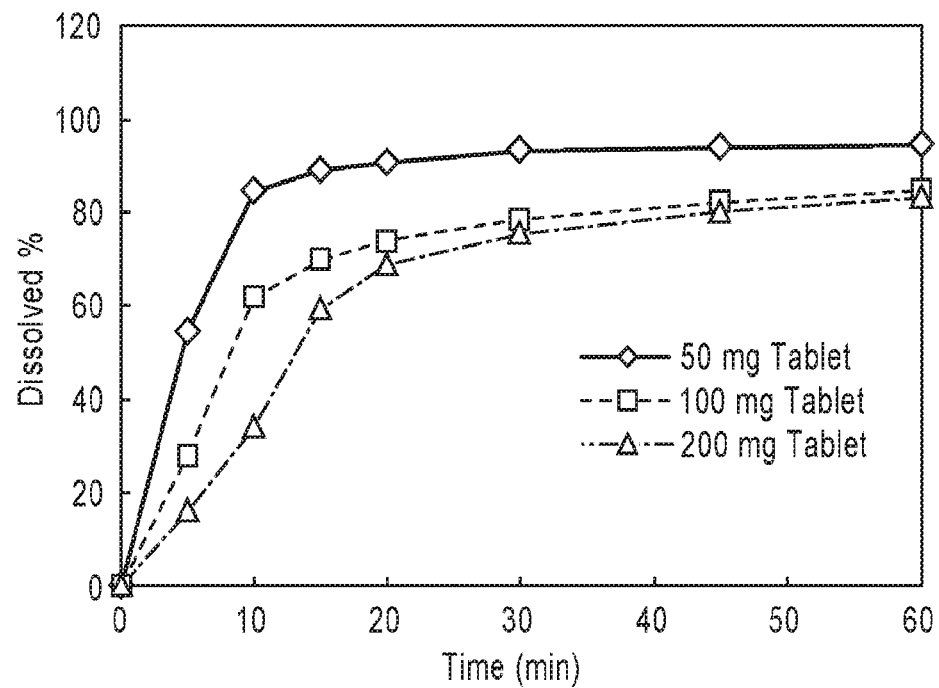
FIG. 9 is a plot showing dissolution profiles of EPZ-6438 50 mg, 100 mg, and 200 mg tablets (n=6, Average), Paddle method (Apparatus 2 of USP<711>), pH 4.5 acetate buffer, 900 ml, 50 rpm.
Figure 10:
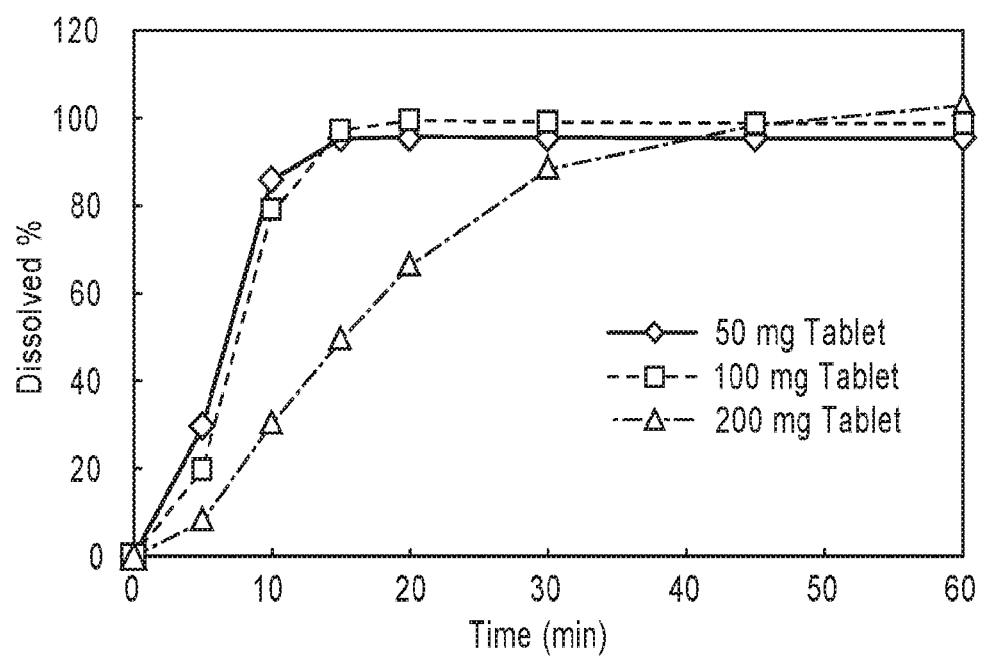
FIG. 10 is a plot showing dissolution profiles of EPZ-6438 50 mg, 100 mg, and 200 mg Tablets (n=6, Average), Paddle method (Apparatus 2 of USP<711>), 0.1N HCl, 900 ml, 50 rpm.
Figure 11:
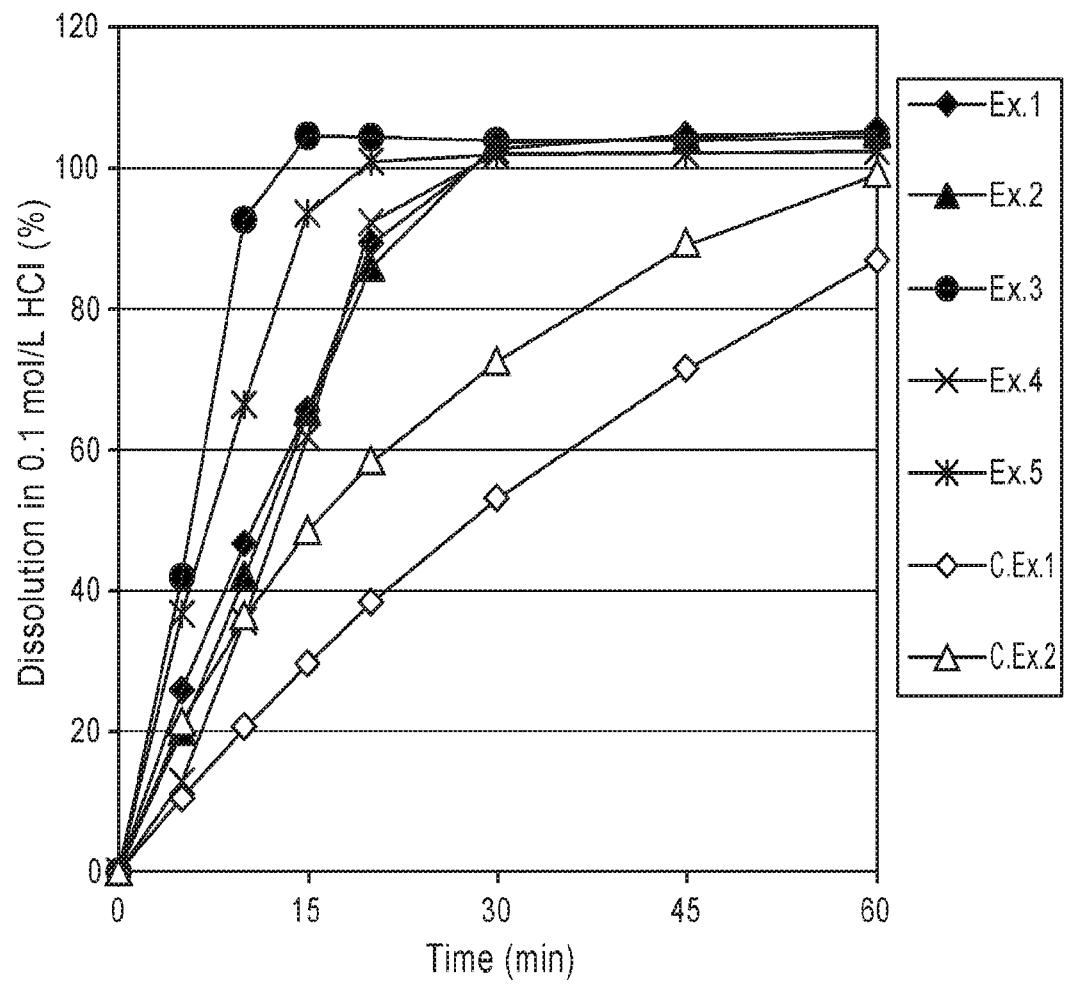
FIG. 11 is a plot showing dissolution profiles of different formulations of EPZ-6438 (n=2, Average), Paddle method (Apparatus 2 of USP<711>), 0.1N HCl, 900 ml, 50 rpm.
Figure 12:
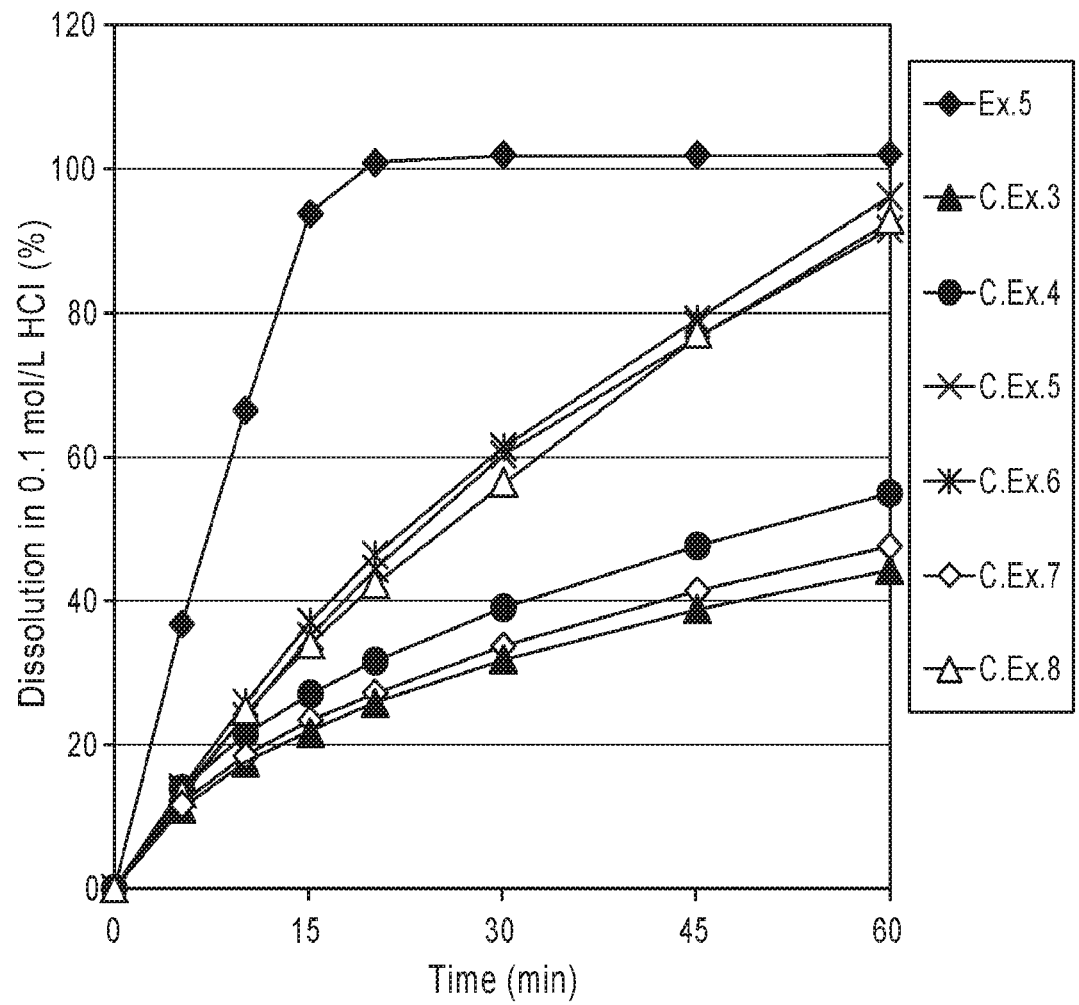
FIG. 12 is a plot showing dissolution profiles of different formulations of EPZ-6438 (n=2, Average), Paddle method (Apparatus 2 of USP<711>), 0.1N HCl, 900 ml, 50 rpm.
Figure 13:
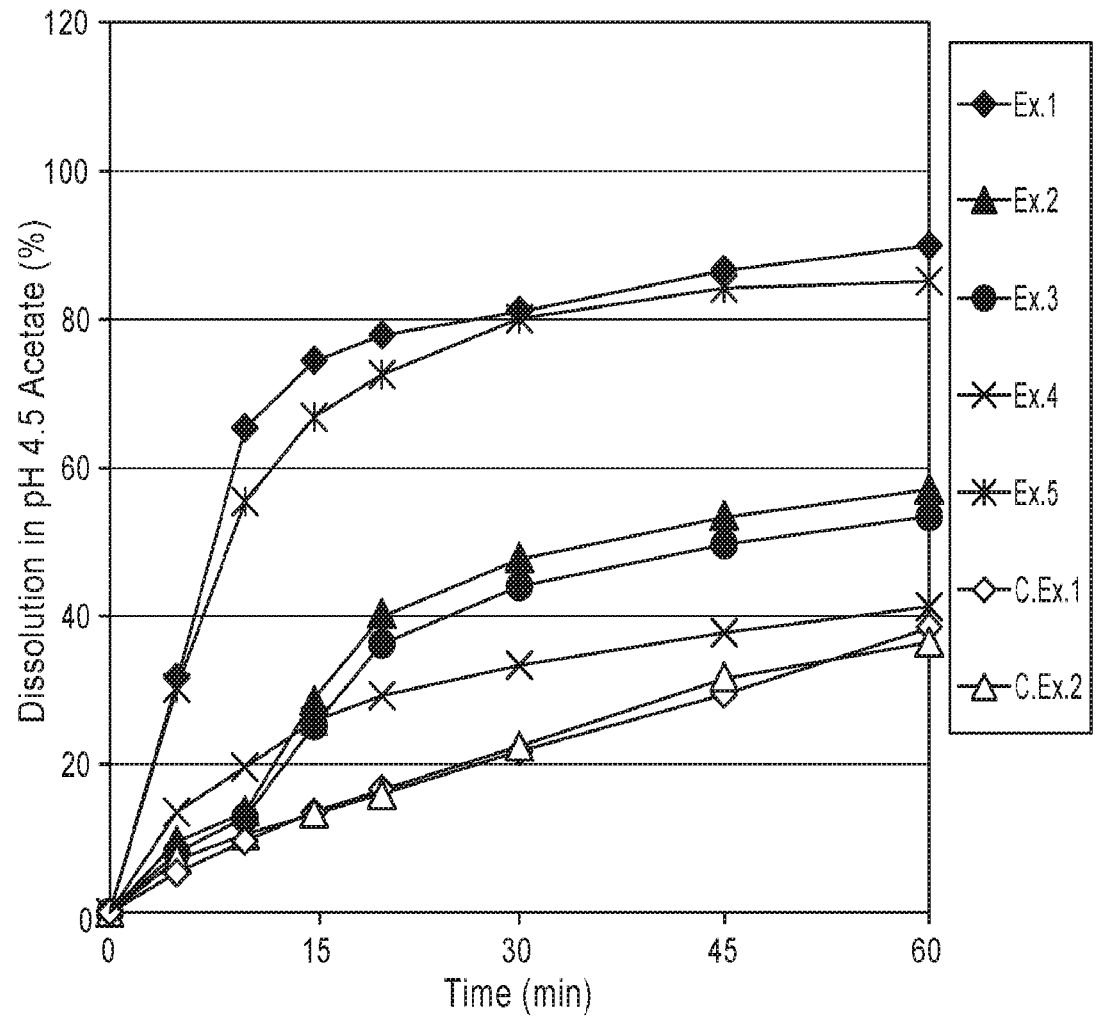
FIG. 13 is a plot showing dissolution profiles of different formulations of EPZ-6438 (n=2, Average), Paddle method (Apparatus 2 of USP<711>), pH 4.5 acetate buffer, 900 ml, 50 rpm.
Figure 14:
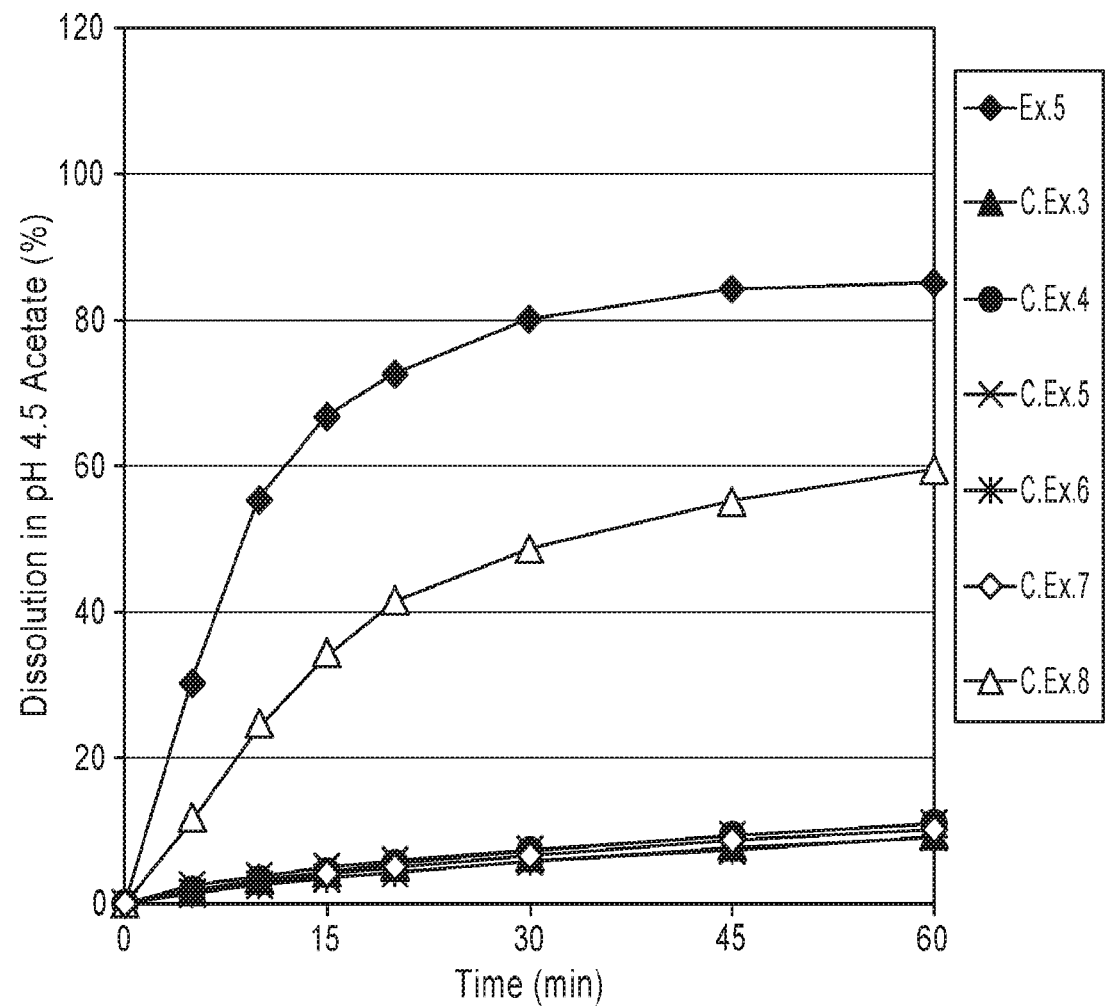
FIG. 14 is a plot showing dissolution profiles of different formulations of EPZ-6438 (n=2, Average), Paddle method (Apparatus 2 of USP<711>), pH 4.5 acetate buffer, 900 ml, 50 rpm.
Figure 15B:
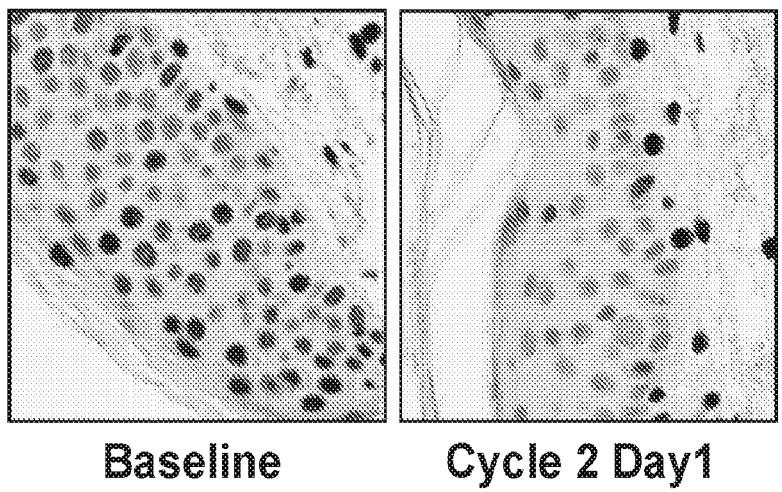
FIG. 15B is a series of pictures demonstrating EPZ-6438 pharmacodynamics in skin.
Figure 15C:
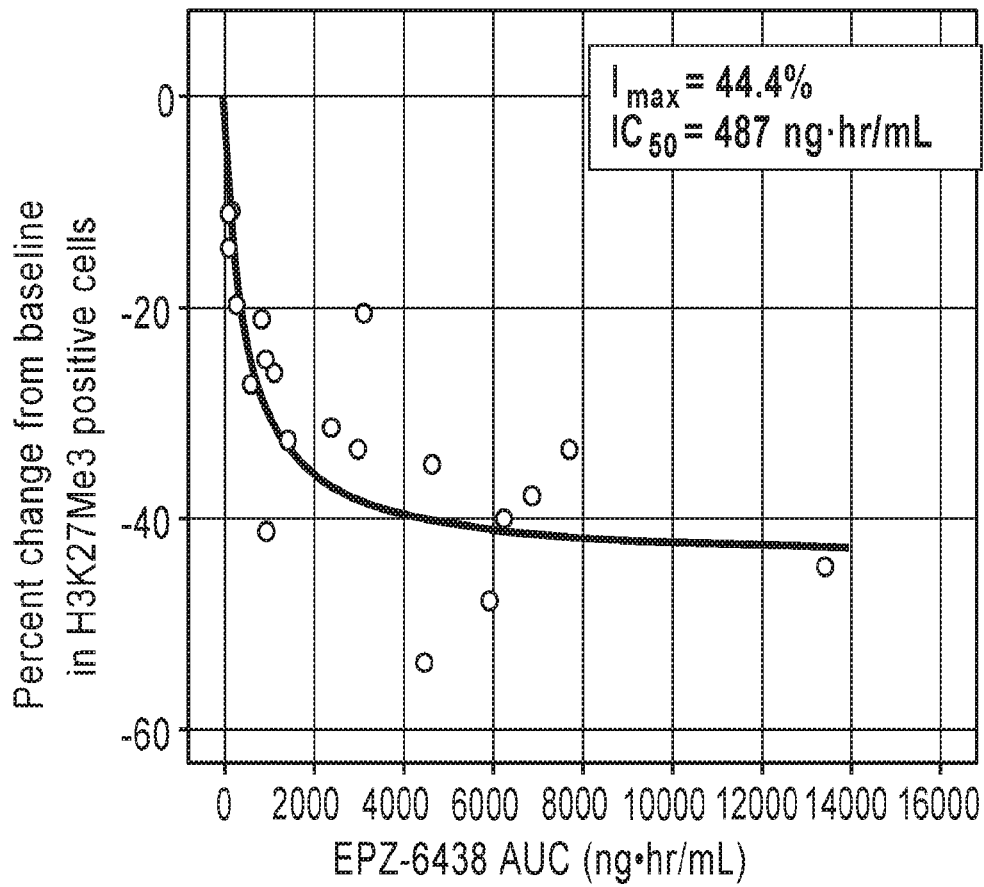
FIG. 15C is a plot demonstrating the correlation between inhibition of histone methylation and EPZ-6438 exposure.
Figure 16C:
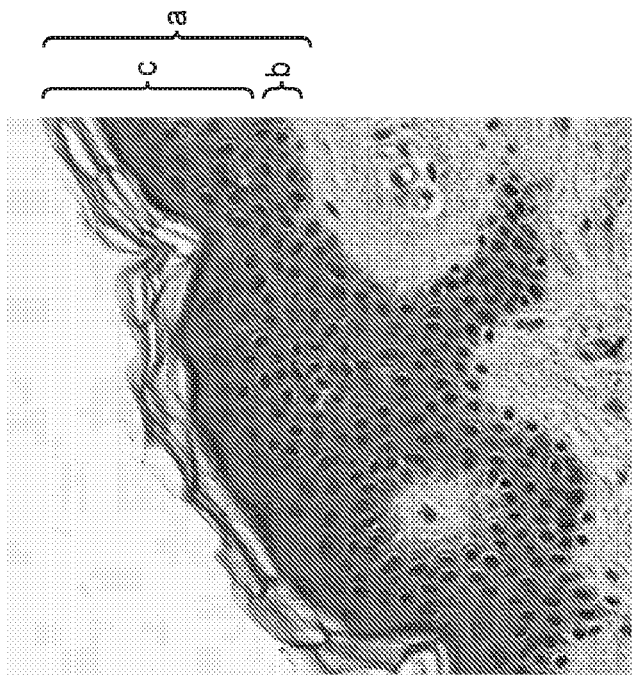
Figure 16F:
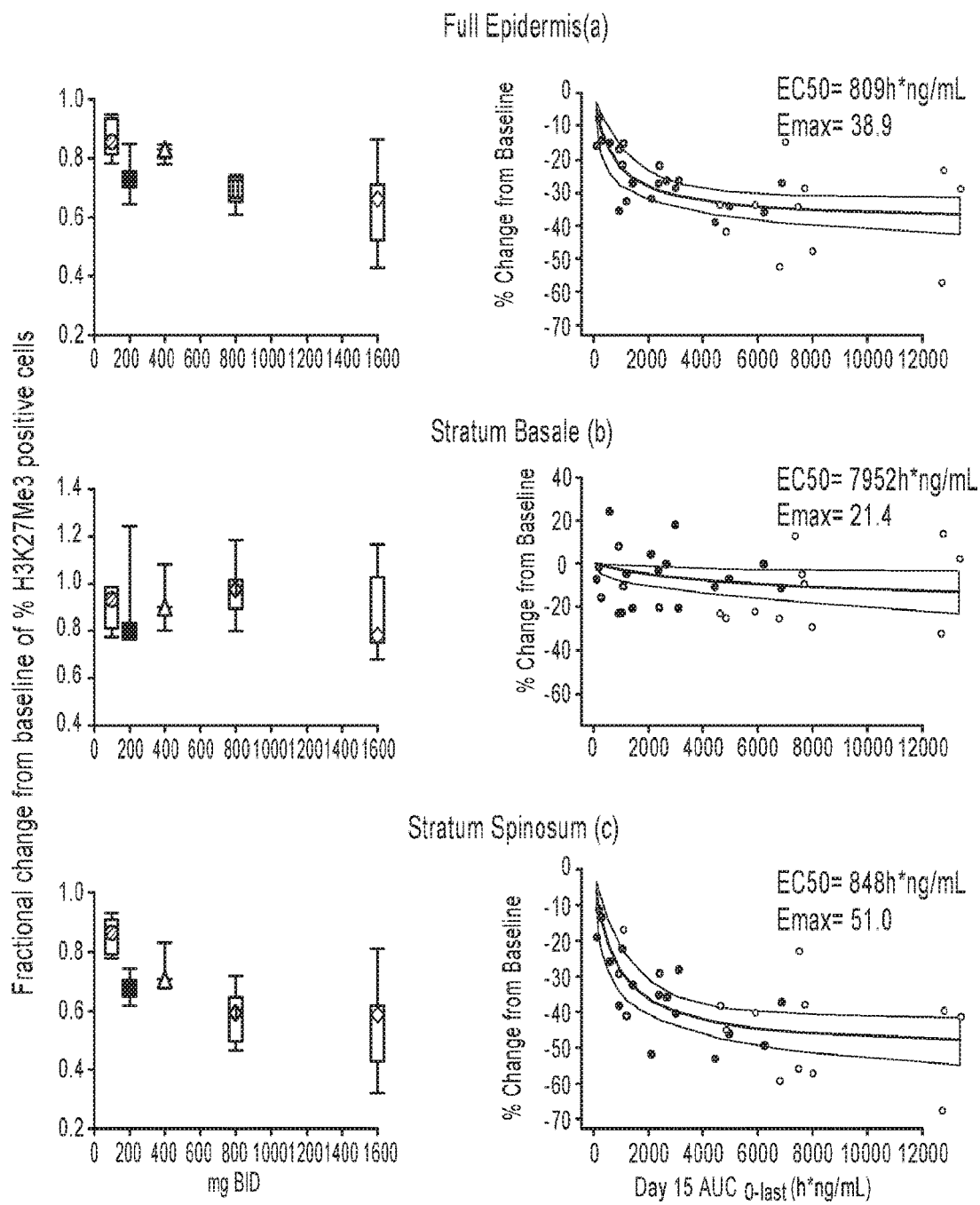

Dissolution tests were conducted with tablets containing Compound 1 HBr with strength equivalent to 50 mg, 100 mg, and 200 mg EPZ-6438 with an industry standard apparatus under standard test conditions. FIGS. 9 and 10 provide the dissolution profiles under different conditions.

Example 3 Preparation of Formulation Nos. 1-5 and Comparative Examples 1-8

The components used for sample preparation are listed in Table 4 below.

TABLE 4

Component list

| Component | Vendor | Grade/Product Name |
|---|---|---|
| EPZ-6438 Drug Substance (Hydrobromide Salt) | Eisai | |
| Lactose Monohydrate | DMV-Fonterra Excipients | Pharmatose 200M |
| Hydroxypropylcellulose | Nippon Soda | SL Type |
| Low-substituted Hydroxypropylcellulose | Shin-Etsu Chemical | LH21 Type |
| Sodium Starch Glycolate | JRS Pharma | Explotab, Type A |
| Carmellose Calcium | Gotoku Chemical | E.C.G-505 |
| Partly Pregelatinized Starch | Asahi Kasei Chemicals | PC-10 Type |
| Croscarmellose Sodium | DSP Gokyo food & Chemical | Ac-Di-Sol |
| Crospovidone | International Specialty Products | XL10 Type |
| Carmellose | Gotoku Chemical | NS-300 Type |
| Microcrystalline Cellulose | Asahi Kasei Chemicals | UF702 Type |
| Light Anhydrous Silicic Acid | Nippon Aerosil | Aerosil 200 |
| Corn Starch | Nihon Shokuhin Kako | |
| Magnesium Aluminometasilicate | Fuji chemical industry Co., Ltd. | Neusilin US2 |
| Dried Methacrylic Acid Copolymer LD | Evonik Industries | Eudragit L100-55 |
| Hydroxypropyl Starch | Frued | HPS-101(W) |
| Magnesium Stearate | Mallinckrodt Japan | |

Listed in Table 5 and Table 6 below are the components of Formulation Nos. 1-5 (referred to as "Ex. 1" through "Ex. 5" in Tables 5-6) and those of Comparative Examples 1~8 (referred to as "C.Ex.1" through "C.Ex.8" in Tables 5-6), as well as the amount of each component in each formulation sample.

TABLE 5

(50 tablets scale)

| | Component | Formulation (mg/tablet) | | | | | |
|---|---|---|---|---|---|---|---|
| | | Ex. 1 | Ex. 2 | Ex. 3 | Ex. 4 | C. Ex. 1 | C. Ex. 2 |
| Intra-Granules | EPZ-6438 Drug Substance (Hydrobromide Salt)[a] | 231.7 | 231.7 | 231.7 | 231.7 | 231.7 | 231.7 |
| | Lactose Monohydrate | 64.7 | 64.7 | 64.7 | 64.7 | 64.7 | 64.7 |
| | Hydroxypropylcellulose | 16.0 | 16.0 | 16.0 | 16.0 | 16.0 | 16.0 |
| | Sodium Starch Glycolate | 40.0 | | | | | |
| | Carmellose Calcium | | 40.0 | | | | |
| | Croscarmellose Sodium | | | 40.0 | | | |
| | Low-substituted Hydroxypropylcellulose | | | | 40.0 | | |

TABLE 5-continued (50 tablets scale)

| | | Formulation (mg/tablet) | | | | | |
|---|---|---|---|---|---|---|---|
| | Component | Ex. 1 | Ex. 2 | Ex. 3 | Ex. 4 | C. Ex. 1 | C. Ex. 2 |
| Out of Granules | Partly Pregelatinized Starch | | | | | 40.0 | |
| | Crospovidone | | | | | | 40.0 |
| | Sodium Starch Glycolate | 40.0 | | | | | |
| | Carmellose Calcium | | 40.0 | | | | |
| | Croscarmellose Sodium | | | 40.0 | | | |
| | Low-substituted Hydroxypropylcellulose | | | | 40.0 | | |
| | Partly Pregelatinized Starch | | | | | 40.0 | |
| | Crospovidone | | | | | | 40.0 |
| | Magnesium Stearate | 7.6 | 7.6 | 7.6 | 7.6 | 7.6 | 7.6 |
| | Total Weight | 400.0 | 400.0 | 400.0 | 400.0 | 400.0 | 400.0 |

[a] As is % (purity as free base) is 86.3%. Equivalent to 200 mg of EPZ-6438 free base.

TABLE 6

(12.5 tablets scale)

| | | Formulation (mg/tablet) | | | | | | |
|---|---|---|---|---|---|---|---|---|
| | Component | Ex. 5 | C. Ex. 3 | C. Ex. 4 | C. Ex. 5 | C. Ex. 6 | C. Ex. 7 | C. Ex. 8 |
| Intra-Granules | EPZ-6438 Drug Substance (Hydrobromide Salt)[a] | 231.7 | 231.7 | 231.7 | 231.7 | 231.7 | 231.7 | 231.7 |
| | Lactose Monohydrate | 64.7 | 64.7 | 64.7 | 64.7 | 64.7 | 64.7 | 64.7 |
| | Hydroxypropyl cellulose | 16.0 | 16.0 | 16.0 | 16.0 | 16.0 | 16.0 | 16.0 |
| | Carmellose | 40.0 | | | | | | |
| | Microcrystalline Cellulose | | 40.0 | | | | | |
| | Light Anhydrous Silicic Acid | | | 10.0 | | | | |
| | Corn Starch | | | | 40.0 | | | |
| | Magnesium Aluminometa Silicate | | | | | 40.0 | | |
| | Dried Methacrylic Acid Copolymer LD | | | | | | 40.0 | |
| | Hydroxypropyl Starch | | | | | | | 40.0 |
| Out of Granules | Carmellose | 40.0 | | | | | | |
| | Microcrystalline Cellulose | | 40.0 | | | | | |
| | Light Anhydrous Silicic Acid | | | 10.0 | | | | |
| | Corn Starch | | | | 40.0 | | | |
| | Magnesium Aluminometa Silicate | | | | | 40.0 | | |
| | Dried Methacrylic Acid Copolymer LD | | | | | | 40.0 | |
| | Hydroxypropyl Starch | | | | | | | 40.0 |
| | Magnesium Stearate | 7.6 | 7.6 | 7.6 | 7.6 | 7.6 | 7.6 | 7.6 |
| | Total Weight | 400.0 | 400.0 | 340.0 | 400.0 | 400.0 | 400.0 | 400.0 |

[a] As is % (purity as free base) is 86.3%. Equivalent to 200 mg of EPZ-6438 free base.

Formulation No. 1 was prepared according to the following method. Other samples were prepared using the method similar to that for Formulation No. 1 except for the different wet-granulation scale and/or the different components and their amounts. The wet-granulation process of the samples shown in Table 5 was executed at 50 tablets scale. The granulation process of the samples shown in Table 6 was executed at 12.5 tablets scale. The weighed amount of components were calculated based on the wet-granulation scale and the formulation shown in Tables 5 and 6.

Preparation of Formulation No. 1

11.59 g of EPZ-6438 drug substance, 3.23 g of lactose monohydrate, 0.80 g of hydroxypropylcellulose and 2.00 g of sodium starch glycolate were mixed using mortar and pestle. The mixture was wet-granulated using mortar and pestle with gradually adding appropriate amount of purified water. The wet-granules were dried using thermostatic oven set at 70° C. The dried granules were passed through a sieve with 710 μm opening. 40.0 mg of sodium starch glycolate and 7.6 mg of magnesium stearate per 352.4 mg of the sieved granules were added to the sieved granules, and the components were lubricated by shaking in a glass vial. The lubricated granules equivalent to one tablet were compressed at 1450 kgf using single-punch tableting equipped with 10.0 mm diameter punch, and the tablet containing 200 mg of EPZ-6438 drug substance as free base was obtained.

Example 4 Dissolution Tests

The dissolution test was executed using Apparatus 2 (paddle method) according to <711> Dissolution of USP 37th. 0.1 mol/L HCl solution and pH 4.5 50 mmol/L acetate buffer were selected as dissolution medium, and prepared according to USP 37th. The dissolution test conditions are summarized in Table 7. The samples were periodically collected from the vessels at pre-determined time after starting the dissolution test, and filtered through UHE-1400 filter with approximately 20 μm opening. The standard solution was prepared near a concentration corresponding to 100% dissolution by dissolving EPZ-6438 drug substance in the dissolution medium. The absorbance of the filtered samples and the standard solution were measured by spectrophotometer, and the dissolution rates were calculated based on the absorbance and the concentration of the standard solution.

TABLE 7

| Parameter | Condition |
|---|---|
| Dissolution Medium | 0.1 mol/L HCl Solution or pH 4.5 50 mmol/L Acetate Buffer |
| Medium Amount | 900 mL |
| Medium Temperature | 37° C. |
| Paddle Speed | 50 rpm |
| Sampling Time | 5, 10, 15, 20, 30, 45 and 60 min |
| Pre-Treatment Filter | UHE-1400 or Equivalent (Dainippon Seiki, Approx. 20 μm opening) |
| Measurement Wavelength | 324 nm |
| Reference Wavelength | 650 nm |
| Light Path Length | 10 mm |

Dissolution Test Results

Dissolution test was executed using 2 vessels per each sample, and the average dissolution rate was shown in Tables 8-9 and FIGS. 11-14. Dissolution test results in 0.1 mol/L HCl solution were shown in Table 8 and FIGS. 11-12. Dissolution test results in pH 4.5 acetate buffer were shown in Table 9 and FIGS. 13-14.

TABLE 8

| | Dissolution in 0.1 mol/L HCl (%) | | | | | | | |
|---|---|---|---|---|---|---|---|---|
| | 0 min | 5 min | 10 min | 15 min | 20 min | 30 min | 45 min | 60 min |
| Ex. 1 | 0.0 | 25.9 | 46.8 | 65.7 | 89.3 | 103.1 | 104.6 | 105.3 |
| Ex. 2 | 0.0 | 19.9 | 42.2 | 65.4 | 85.9 | 103.9 | 104.5 | 104.9 |
| Ex. 3 | 0.0 | 42.0 | 92.7 | 104.6 | 104.5 | 104.1 | 103.9 | 104.3 |
| Ex. 4 | 0.0 | 12.8 | 35.6 | 61.9 | 92.3 | 102.3 | 102.2 | 102.4 |
| Ex. 5 | 0.0 | 36.6 | 66.4 | 93.5 | 100.8 | 101.8 | 101.8 | 102.0 |
| C. Ex. 1 | 0.0 | 10.6 | 20.5 | 29.7 | 38.3 | 53.1 | 71.6 | 87.0 |
| C. Ex. 2 | 0.0 | 21.4 | 36.4 | 48.5 | 58.3 | 72.5 | 89.4 | 99.1 |
| C. Ex. 3 | 0.0 | 11.2 | 17.4 | 21.7 | 25.7 | 31.8 | 38.8 | 44.3 |
| C. Ex. 4 | 0.0 | 13.8 | 21.3 | 26.9 | 31.7 | 39.0 | 47.8 | 54.9 |
| C. Ex. 5 | 0.0 | 12.1 | 23.9 | 35.2 | 44.4 | 60.3 | 78.3 | 91.7 |
| C. Ex. 6 | 0.0 | 13.6 | 25.9 | 37.0 | 46.3 | 61.4 | 79.0 | 96.0 |
| C. Ex. 7 | 0.0 | 11.6 | 18.4 | 23.2 | 27.0 | 33.6 | 41.3 | 47.5 |
| C. Ex. 8 | 0.0 | 13.4 | 24.6 | 34.0 | 42.3 | 56.5 | 76.8 | 92.9 |

TABLE 9

| | Dissolution in pH 4.5 Acetate (%) | | | | | | | |
|---|---|---|---|---|---|---|---|---|
| | 0 min | 5 min | 10 min | 15 min | 20 min | 30 min | 45 min | 60 min |
| Ex. 1 | 0.0 | 31.6 | 65.3 | 74.4 | 77.9 | 81.1 | 86.7 | 89.9 |
| Ex. 2 | 0.0 | 9.4 | 13.6 | 28.3 | 40.3 | 47.7 | 53.5 | 57.0 |
| Ex. 3 | 0.0 | 8.0 | 12.9 | 25.2 | 36.4 | 44.0 | 49.7 | 53.5 |
| Ex. 4 | 0.0 | 13.7 | 19.5 | 25.7 | 29.2 | 33.3 | 37.7 | 41.2 |
| Ex. 5 | 0.0 | 30.2 | 55.3 | 66.8 | 72.5 | 80.1 | 84.1 | 85.0 |
| C. Ex. 1 | 0.0 | 5.4 | 9.8 | 13.4 | 16.7 | 21.7 | 29.5 | 38.4 |
| C. Ex. 2 | 0.0 | 7.1 | 10.5 | 13.4 | 16.1 | 22.4 | 31.6 | 36.5 |
| C. Ex. 3 | 0.0 | 1.9 | 3.3 | 4.2 | 5.1 | 6.4 | 8.2 | 9.4 |
| C. Ex. 4 | 0.0 | 1.9 | 3.3 | 4.5 | 5.5 | 7.2 | 9.4 | 11.1 |

TABLE 9-continued

| | Dissolution in pH 4.5 Acetate (%) | | | | | | |
|---|---|---|---|---|---|---|---|
| | 0 min | 5 min | 10 min | 15 min | 20 min | 30 min | 45 min | 60 min |
| C. Ex. 5 | 0.0 | 2.4 | 3.8 | 4.9 | 5.8 | 7.5 | 9.4 | 11.1 |
| C. Ex. 6 | 0.0 | 1.3 | 2.5 | 3.4 | 4.2 | 5.7 | 7.5 | 9.1 |
| C. Ex. 7 | 0.0 | 1.6 | 2.8 | 4.0 | 4.9 | 6.6 | 8.6 | 10.2 |
| C. Ex. 8 | 0.0 | 11.7 | 24.6 | 34.3 | 41.5 | 48.7 | 55.1 | 59.7 |

Formulation Nos. 1-5 dissolved rapidly in 0.1 mol/L HCl solution, and the average dissolution rate reached more than 80% at 30 minutes. In addition, the average dissolution rate in pH 4.5 acetate buffer of Formulation Nos. 1-4 reached 40% or higher at 30 minutes. Especially, Formulation Nos. 1 and 5 dissolved 80% or more at 30 minutes in pH 4.5 acetate buffer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A solid pharmaceutical formulation comprising N-((4,6-dimethyl-2-oxo-1,2-dihydropyridin-3-yl) methyl)-5-(ethyl(tetrahydro-2H-pyran-4-yl)amino)-4-methyl-4'-(morpholinomethyl)-[1,1'-biphenyl]-3-carboxamide:

("Compound 1")

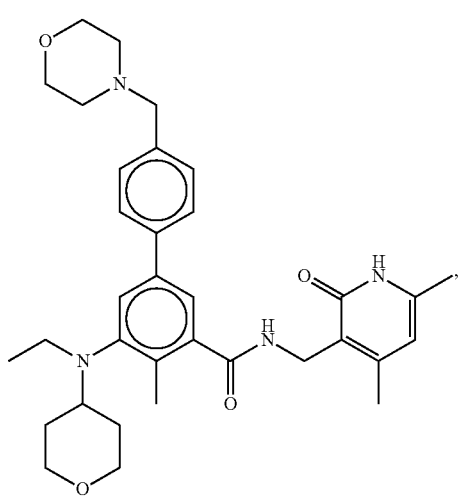

in an amount of about 40-60 wt. %, or a salt of Compound 1 in an amount equivalent to about 40-60 wt. % of Compound 1, or a combination of Compound 1 and a salt of Compound 1 wherein the combination is present in an amount equivalent to about 40-60 wt. % of Compound 1;
lactose monohydrate in an amount of about 10-20 wt. %;
low-substituted hydroxypropyl cellulose in an amount of about 11-19 wt. %;
sodium starch glycolate in an amount of about 3-7 wt. %;
hydroxypropyl cellulose in an amount of about 1-10 wt. %;
magnesium stearate in an amount of about 0.5-5 wt. %; and
a coating composition in an amount of about 1-10 wt. %.

in an amount of about 49 wt. %, or a salt of Compound 1 in an amount equivalent to about 49 wt. % of Compound 1, or a combination of Compound 1 and a salt of Compound 1 wherein the combination is present in an amount equivalent to about 49 wt. % of Compound 1;
lactose monohydrate in an amount of about 17 wt. %;
low-substituted hydroxypropyl cellulose in an amount of about 15 wt. %;
sodium starch glycolate in an amount of about 5 wt. %;
hydroxypropyl cellulose in an amount of about 4 wt. %; and
magnesium stearate in an amount of about 2 wt. %.

2. A solid pharmaceutical formulation consisting of:
N-((4,6-dimethyl-2-oxo-1,2-dihydropyridin-3-yl) methyl)-5-(ethyl(tetrahydro-2H-pyran-4-yl)amino)-4-methyl-4'-(morpholinomethyl)-[1,1'-biphenyl]-3-carboxamide:

("Compound 1")

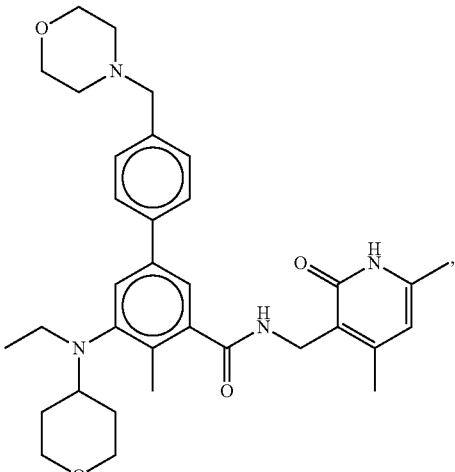

3. The solid pharmaceutical formulation of claim 2, wherein the coating composition comprises hypromellose, talc, macrogol, titanium dioxide, and iron (III) oxide.

4. The solid pharmaceutical formulation of claim 1, further comprising a coating composition.

5. The solid pharmaceutical formulation of claim 4, wherein the coating composition comprises hypromellose, talc, macrogol, titanium dioxide, and iron (III) oxide.

6. The solid pharmaceutical formulation of claim 1, wherein the pharmaceutical composition comprises Compound 1 in an amount of about 49 wt. %.

7. The solid pharmaceutical formulation of claim 1, wherein the pharmaceutical composition comprises a salt of Compound 1 in an amount equivalent to about 49 wt. % of Compound 1.

8. The solid pharmaceutical formulation of claim 7, wherein the salt of Compound 1 is a hydrobromide salt of Compound 1.

9. The solid pharmaceutical formulation of claim 1, wherein the pharmaceutical composition comprises a combination of Compound 1 and a salt of Compound 1 wherein the combination is present in an amount equivalent to about 49 wt. % of Compound 1.

10. The solid pharmaceutical formulation of claim 9, wherein the salt of Compound 1 is a hydrobromide salt of Compound 1.

11. The solid pharmaceutical formulation of claim 2, consisting of
Compound 1 in an amount of about 49 wt. %;
lactose monohydrate in an amount of about 10-20 wt. %;
low-substituted hydroxypropyl cellulose in an amount of about 11-19 wt. %;
sodium starch glycolate in an amount of about 3-7 wt. %;
hydroxypropyl cellulose in an amount of about 1-10 wt. %;
magnesium stearate in an amount of about 0.5-5 wt. %; and
a coating composition in an amount of about 1-10 wt. %.

12. The solid pharmaceutical formulation of claim 2, consisting of
a salt of Compound 1 in an amount equivalent to about 49 wt. % of Compound 1;
lactose monohydrate in an amount of about 10-20 wt. %;
low-substituted hydroxypropyl cellulose in an amount of about 11-19 wt. %;
sodium starch glycolate in an amount of about 3-7 wt. %;
hydroxypropyl cellulose in an amount of about 1-10 wt. %;
magnesium stearate in an amount of about 0.5-5 wt. %; and
a coating composition in an amount of about 1-10 wt. %.

13. The solid pharmaceutical formulation of claim 12, wherein the salt of Compound 1 is a hydrobromide salt of Compound 1.

14. The solid pharmaceutical formulation of claim 2, consisting of
a combination of Compound 1 and a salt of Compound 1 wherein the combination is present in an amount equivalent to about 49 wt. % of Compound 1;
lactose monohydrate in an amount of about 10-20 wt. %;
low-substituted hydroxypropyl cellulose in an amount of about 11-19 wt. %;
sodium starch glycolate in an amount of about 3-7 wt. %;
hydroxypropyl cellulose in an amount of about 1-10 wt. %;
magnesium stearate in an amount of about 0.5-5 wt. %; and
a coating composition in an amount of about 1-10 wt. %.

15. The solid pharmaceutical formulation of claim 14, wherein the salt of Compound 1 is a hydrobromide salt of Compound 1.

16. The solid pharmaceutical formulation of claim 2, consisting of
Compound 1 in an amount of about 49 wt. %;
lactose monohydrate in an amount of about 17 wt. %;
low-substituted hydroxypropyl cellulose in an amount of about 15 wt. %;
sodium starch glycolate in an amount of about 5 wt. %;
hydroxypropyl cellulose in an amount of about 4 wt. %;
magnesium stearate in an amount of about 2 wt. %; and
a coating composition in an amount of about 4 wt. %.

17. The solid pharmaceutical formulation of claim 2, consisting of
a salt of Compound 1 in an amount equivalent to about 49 wt. % of Compound 1;
lactose monohydrate in an amount of about 17 wt. %;
low-substituted hydroxypropyl cellulose in an amount of about 15 wt. %;
sodium starch glycolate in an amount of about 5 wt. %;
hydroxypropyl cellulose in an amount of about 4 wt. %;
magnesium stearate in an amount of about 2 wt. %; and
a coating composition in an amount of about 4 wt. %.

18. The solid pharmaceutical formulation of claim 17, wherein the salt of Compound 1 is a hydrobromide salt of Compound 1.

19. The solid pharmaceutical formulation of claim 2, consisting of
a combination of Compound 1 and a salt of Compound 1 wherein the combination is present in an amount equivalent to about 49 wt. % of Compound 1;
lactose monohydrate in an amount of about 17 wt. %;
low-substituted hydroxypropyl cellulose in an amount of about 15 wt. %;
sodium starch glycolate in an amount of about 5 wt. %;
hydroxypropyl cellulose in an amount of about 4 wt. %;
magnesium stearate in an amount of about 2 wt. %; and
a coating composition in an amount of about 4 wt. %.

20. The solid pharmaceutical formulation of claim 19, wherein the salt of Compound 1 is a hydrobromide salt of Compound 1.

* * * * *

UNITED STATES PATENT AND TRADEMARK OFFICE
CERTIFICATE OF CORRECTION

PATENT NO. : 10,786,511 B2
APPLICATION NO. : 15/527375
DATED : September 29, 2020
INVENTOR(S) : Keilhack et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 32 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*